United States Patent [19]

Kajikawa et al.

[11] Patent Number: 6,051,533
[45] Date of Patent: Apr. 18, 2000

[54] FORMULATIONS HAVING ENHANCED WATER DISSOLUTION

[75] Inventors: Akira Kajikawa; Masuo Kuchikata, both of Ibaraki, Japan; Ronald O. Richardson, Ellisville, Mo.; Tatsuo Sato, Tokyo, Japan

[73] Assignee: Monsanto Company, St. Louis, Mo.

[21] Appl. No.: 08/935,213

[22] Filed: Sep. 22, 1997

Related U.S. Application Data

[63] Continuation of application No. 08/500,711, Jul. 11, 1995, abandoned, which is a continuation of application No. 07/673,032, Mar. 21, 1991, abandoned, which is a continuation of application No. 07/339,448, Apr. 17, 1989, abandoned.

[51] Int. Cl.⁷ .......................... A01N 57/00; A01N 25/00; A01N 25/12; A01N 25/30
[52] U.S. Cl. ........................................ 504/206; 71/DIG. 1
[58] Field of Search ...................... 504/206, 116, 504/189; 71/DIG. 1; 424/405, 408, 409, 489, 497

[56] References Cited

U.S. PATENT DOCUMENTS

| | | | |
|---|---|---|---|
| 3,799,758 | 3/1974 | Franz | 71/86 |
| 4,936,901 | 6/1990 | Surgant, Sr. et al. | 71/86 |
| 5,612,285 | 3/1997 | Arnold | 504/206 |
| 5,656,572 | 8/1997 | Kuchikata et al. | 504/206 |
| 5,693,593 | 12/1997 | Arnold | 504/206 |

FOREIGN PATENT DOCUMENTS

| | | |
|---|---|---|
| 2045223 | 6/1991 | Canada . |
| 62-175408 | 8/1987 | Japan . |
| 64-25702 | 1/1989 | Japan . |

OTHER PUBLICATIONS

"Pesticide—Design and Guideline for Development," pp. 1019–1020, editd by I. Yamamoto et al., published Mar. 31, 1979 by Soft Science Co.
Chemical Abstracts 102:144741 (1985).
Farm Chemicals Handbook '87, Meister Publishing Co., 1987, Willoughby (Ohio), p. C–131.
Derwent Abstract AN: C87–107442, 1987.
Union Carbide Corp., Surface Active Polymers. 1983.
Union Carbide Corp., Silicones for the Agricultural Industry. 1984.
Balmeaves, John M., Proceedings of the Thirty Eighth New Zealand Weed and Pest Control Conference, 1985. pp 98–101.
Jansen, L.L. "Enhancement of Herbicides by Silicon Surfactants," Weed Science, 1973, vol. 21(2), pp 130–135.

*Primary Examiner*—John Pak
*Attorney, Agent, or Firm*—James C. Forbes; Arnold White & Durkee

[57] ABSTRACT

This invention relates to dry, water soluble, pesticidally acceptable particulate compositions, to a method of use thereof for killing or controlling pests including weeds and to a process for preparing such compositions. This invention also relates to dry, water soluble and/or water dispersible, pesticidally acceptable particulate herbicidal compositions containing one or more herbicides, a herbicidal method of use thereof and to a process for preparing such compositions. The dissolution or dispersible rates of particulate pesticidal compositions in water are enhanced by the presence of a small but effective amount of an organosilicone block copolymer wetting agent or a fluorocarbon wetting agent.

4 Claims, No Drawings

FORMULATIONS HAVING ENHANCED WATER DISSOLUTION

This application is a continuation of application Ser. No. 08/500,711, filed Jul. 11, 1995, now abandoned, which is a continuation of application Ser. No. 07/673,032, filed Mar. 21, 1991, now abandoned, which is a continuation of application Ser. No. 07/339,448, filed Apr. 17, 1989, now abandoned.

FIELD OF THE INVENTION

This invention relates to a pesticide-containing formulation in particulate form having enhanced water dissolution and to a process for preparing such compositions. More particularly, this invention relates to dry, water soluble or water dispersible, agriculturally acceptable herbicidal compositions containing one or more herbicides, to herbicidal methods of use of such compositions and to a process for preparing such compositions.

DESCRIPTION OF THE PRIOR ART

N-phosphonomethylglycine, whose common name is glyphosate, is well known in the art as a highly effective herbicide. It is also -known that glyphosate, an organic acid, has low solubility in water. Glyphosate is typically formulated as a water-soluble salt, especially as the mono-isopropylamine (IPA) salt to kill or control weeds or plants. Glyphosate is sold commercially as an aqueous concentrate in the form of its IPA salt by Monsanto Company under the trademark Roundup.

Various salts of glyphosate, methods for preparing salts of glyphosate, formulations of glyphosate and methods of use for killing and controlling weeds and plants are disclosed in U.S. Pat. Nos. 3,799,758 and 4,405,531 issued to John E. Franz on Mar. 26, 1974 and Sep. 20, 1983, respectively. Other U.S. Patents which disclose salts of glyphosate include U.S. Pat. No. 4,315,765 issued to George B. Large on Feb. 16, 1982, U.S. Pat. No. 4,507,250 issued to Izak Bakel on Mar. 26, 1985, U.S. Pat. No. 4,397,676 issued to Izhak Bakel on Aug. 9, 1983, U.S. Pat. No. 4,481,026 issued to Michael P. Prisbylla on Nov. 6, 1984 and, U.S. Pat. No. 4,140,513 issued to Erhard J. Prill on Feb. 20, 1979. The aforementioned patents are incorporated herein in their entireties by reference thereto.

European Patent Application 0 204 146 discloses a herbicidal composition comprising (a) 2-(4-chloro-2-fluoro 5-propargyloxyphenyl)-5,6,7, 8-tetrahydro-1H-1,2,4-triazolo (1,2-s)pyridazine -1,3, -2H-dione (I), and (b) glyphosate, glufosinate, bialaphos, and/or paraquat or their salts and an inert carrier or diluent.

European Patent Application 0 244 760 discloses an agricultural composition in granular form prepared by introducing to the top of a drying tower, a mixture of the agricultural chemical, an anionic surfactant and optionally one or more additives in the form of a concentrated solution or an aqueous slurry.

Published Japanese patent applications J62175407 and J62175408 disclose a herbicide containing a solid carrier, additives and herbicidal component and having a particle size of 48–150 mesh. Disclosed herbicidal components are [(3-amino-3-carboxy)propyl-1]methylphosphonic acid, N-phosphono-methylglycine, (2-amino-4-methylphosphino-butyral) alanylalanine and their salts.

European Patent Application 0 206 537 discloses a solid, substantially non-hygroscopic, phytoactive composition comprising an intimate mixture of a phytoactive N-phosphonomethyl-N-carboxymethyl compound and a surfactant which is solid at ambient temperatures.

European Patent Application 0 256 608 discloses a method for the preparation of a solid, phytoactive composition comprising the steps of (a) reacting an acid form of a phytoactive N-phosphono-methyl-N-carboxymethyl compound with a liquid amine to form the amine salt of said N-phosphonomethyl-N-carboxymethyl compound, (b) admixing said amine salt of said N-phosphonomethyl-N-carboxymethyl compound with a molten surfactant, the surfactant being solid at ambient temperature and (c) cooling the resulting mixture to a temperature below the melting point of the surfactant to form a composition comprising the surfactant and the amine salt of N-phosphonomethyl-N-carboxylmethyl compound interdispersed in the matrix thereof and which is solid at ambient temperatures.

PCT Publication No. WO 87/04595 discloses a herbicidal water-soluble dry particulate glyphosate formulation comprising the sodium salt of glyphosate and a surface active agent of the formula:

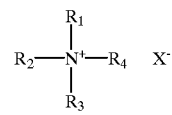

wherein $R_1$ and $R_2$ are independently methyl or ethyl, $R_3$ is methyl, ethyl benzyl or $C_{10}$ to $C_{18}$ alkyl, $R_4$ is $C_{10}$ to $C_{18}$ alkyl and X is chlorine or bromine.

The use of an organosilicone surfactant, such as Silwet® L-77 sold by Union Carbide Company, in tank mixes with commercially purchased Roundup herbicide improves the rainfastness of the resulting formulation of Roundup on some species of weeds.

Monsanto Company sells Pulse brand penetrant (which contains Silwet L-77) for use with Roundup herbicide. The label of Pulse penetrant discloses that the addition of Pulse penetrant can reduce the rainfree period after application of Roundup herbicide for best activity from 4–6 hours to 2 hours on perennial ryegrass when recommended rates of Roundup herbicide and Pulse penetrant are sprayed on dry foliage.

L. Jansen, "Enhancement of Herbicides by Silicone Surfactants" Volume 21, Issue 2 (March) 1983, *WEED SCIENCE,* discloses that in a comparative evaluation of adjuvant effects in eight species, nonionic silicone glycol surfactants enhanced the activity of six herbicides to a greater extent than a standard organic surfactant, whereas cationic amino silicone surfactants enhanced to a lesser extent.

Japanese LOP 145 205-88 discloses an aqueous concentrate herbicidal formulation comprising a water soluble glyphosate salt, ammonium sulfate and a quaternary ammonium salt.

PCT Publication No. WO 87/04,712 discloses a method of preparing a particulate alkali metal salt of N-phosphonomethylglycine which comprises adding a solid alkali metal base with agitation to N-phosphono-methylglycine containing up to 25% water.

Research Disclosure Publication 27161 November 1986 entitled "Novel Glyphosate Acid Wettable Powder Formulation Effective in Control of Weeds" discloses a formulation comprising N-phosphonomethyl-glycine, nonionic surfactant, diatomaceous earth, inorganic salt (e.g., ammonium sulfate) and an anti-foaming agent.

Chemical Abstracts 103: 191395K (1985) Davydov, A. M.; Vechtomova, T. N.; Banzunova, G. G. (USSR). Sashch. Rast. (Moscow) 1985, (9), 40-1 (Russ) discloses that the 36% aq. soln. Utal (I) [96638-41-4] and the 50% wettable powder Fosulen (II) are Soviet brands of glyphosate.

As mentioned above, organosilicones are sold commercially under the trademark Silwet® by Union Carbide. In particularly, SILWET Surfactants L-77, L-720, L-7001, L-7500, L-7600, L-7602, L-7604, L-7605, and L-7607 are exempted by the Environmental Protection Agency (EPA) [40 CRF 180,1001(c)] from the requirement of a residue tolerance, when used in accordance with good agricultural practice as inert ingredients in pesticide formulations applied to growing crops or to raw agricultural commodities after harvest.

SUMMARY OF THE INVENTION

There is provided a novel and useful composition containing a pesticide, including herbicides, insecticides, fungicides and the like, and sufficient silicone copolymer wetting agent, fluoroaliphatic wetting agent or mixtures thereof such that a cylindrical pellet of the composition having a diameter of one millimeter and a length of the three millimeters shaped from the composition becomes essentially fully dissolved or dispersed when tumbled in water in at least 50% quicker or less time than a pellet of the same size and of the same composition but having no such wetting agent.

The amount of wetting agent in the pesticide-containing composition is in the range of about 0.1 to about 5.0% by weight of the composition, preferably in the range of about 0.2 to about 4.0% by weight of the composition.

The invention provides a dry, agriculturally acceptable composition comprising in particulate form a water-dispersible granule, water soluble granule, or water-dispersible powder or water soluble powder (although water soluble granules are preferred) containing a dissolution enhancing amount of an organosilicone and/or fluorochemical wetting agent.

Compositions of this invention may further comprise ammonium sulfate, potassium sulfate, potassium chloride, sodium sulfate, urea, ammonium phosphate mixtures thereof and the like. The composition may optionally include a synergist, quick-burn additive, a humectant, a co-herbicide, a dye, pigment, corrosion inhibitor, thickener, dispersing agent, calcium seguestrant, defoamer, mixtures thereof and like additiments. When employing two or more herbicides in the composition, the composition of this invention may be a water soluble or a water dispersible granule. If at least one of two or more herbicides employed herein is relatively insoluble in water, a water dispersible composition is preferred.

In one embodiment of this invention a process for preparing a composition of this invention, a dry, water soluble or water dispersible, granular, agriculturally acceptable composition is prepared by pan, extrusion, fluid bed (or equivalent) granulation of N-phosphonomethylglycine, or a water soluble salt of N-phosphonomethylglycine, together with the necessary organosilicone and/or fluorochemical wetting agent and optionally with a surfactant.

In another embodiment of this invention, the novel composition is prepared by admixing an agriculturally acceptable salt of N-phosphonomethyl-glycine with one or more liquid or solid surfactants and an organosilicone block copolymer and/or fluoro-chemical wetting agent. The salt preferably is the ammonium salt or an alkali metal salt with sodium being the preferred alkali metal.

In another method of preparing the composition of this invention, one may admix ingredients including an organosilicone wetting agent or a fluoro-chemical wetting agent or mixture thereof with water and thereafter spray dry the resulting admixture to give a granular product.

In another method of preparing the compositions of this invention, one may admix the ingredients including an organosilicone wetting agent or fluorochemical wetting agent or mixture thereof with water and drum dry on a flaking roll and grind the flaked composition to give a granular composition.

Yet another method of preparing the granular compositions of this invention involves admixing glyphosate salt, ammonium bicarbonate, organosilicone wetting agent or fluorochemical wetting agent or mixtures thereof with water, crystallizing, centrifuging and blending in the wetting agent and drying the granular product.

Compositions of the present invention may be optionally mixed with ammonium sulfate and optionally with one or more additional herbicides and thereafter these ingredients blended to form said admixed composition. The order of addition of the ingredients to the starting material, typically glyphosate or a water soluble salt thereof, is not critical. The admixed composition is optionally granulated with equivalent means or in an equivalent manner to form a composition of this invention.

OBJECTS OF THE INVENTION

It is an object of this invention to provide a dry, water soluble and/or water dispersible, pesticide-containing composition and a process for preparing said composition.

It is yet another object of this invention to provide a pesticidal method of use for killing and controlling pests by applying a pesticidally effective amount of a pesticidal composition of the present inventions to the locus of the pest, such as a plant or weed to be killed or controlled.

It is a further object of this invention to provide a dry, water soluble and highly water dispersible agriculturally acceptable herbicidal composition which has relatively low shipping costs, mix compatibility with various co-herbicides, mix compatibility with various additives which can be packaged in low cost, combustible biodegradable containers and is easy to use with minimum user contact with the composition.

These and other objects such as a uniform particle size distribution, high water dissolution noncaking features are achieved in this invention as hereinafter described in more detail.

An advantage offered by this invention is where a worker exposure is an issue. Dry formulations are excellent candidates for packaging in water-soluble bags that would substantially reduce user exposure from handling and mixing.

DETAILED DESCRIPTION OF THE INVENTION

The invention comprises a dry, water soluble or water dispersible, pesticidal composition containing an effective amount of an organosilicone and/or fluorochemical dissolution enhancer or wetting agent such that a pellet of such composition becomes essentially fully dissolved or dispersed in less than about three minutes when tumbled in water and will so dissolve in about one half the time that a similar pellet without the wetting agent would dissolve or disperse under like conditions. The rapid dissolution or dispersion can be formed under low or no sheer.

As employed herein as to the wetting agent, the term "liquid" means a substance in a flowable state at room temperature (about 25° C.) and includes waxes and liquid compositions containing solid surfactants.

The compositions of this invention are typically greater than about 60 mesh and contain the wetting agent in the range from about 0.1% to about 5.0% weight and preferably less than about 2% weight percent water, although greater or lesser amounts of water may be present depending on the composition ingredients.

One preferred class of wetting agent has the average formula

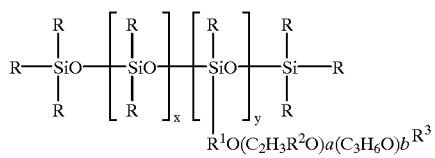

where each R is independently a monovalent hydrocarbyl radical, $R^1$ is a divalent hydrocarbylene radical, $R^2$ is independently hydrogen or a lower hydroxyalkyl radical, $R^3$ is hydrogen or a monovalent hydrocarbyl radical, x, y, a and b are integers independently greater than or equal to zero, with the proviso that a has a sufficient value and b is small enough so that the composition of the invention has the desired dissolution rate of less than five minutes. Preferably in compounds of Formula I, R and $R^3$ are —$CH_3$, $R^1$ is —$C_3H_6$—, $R^2$ is hydrogen, x is zero or one, y is one to five, a is five to 20 and b is zero.

Another preferred class of organosilicone wetting agents has the average formula

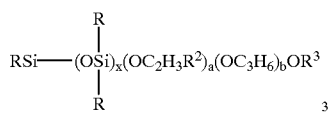

where R, $R^2$, $R^3$, x, a and b are as defined immediately above. Preferably in compounds of Formula II, R and $R^3$ are —$CH_3$, $R^2$ is hydrogen, a is five to 20 and b is zero.

Organosilicones of Formulas I and II above are generally described in the above-mentioned Union Carbide Corp. product literature and in U.S. Pat. Nos. 3,505,377, 3,980,688, and 4,431,789, the disclosures of which are incorporated herein by reference. Several of such ethoxylated wetting agents are available from Union Carbide Corp. as SILWET surface active copolymers. Preferred SILWET surface active copolymers include SILWET L-77, L-7600, L-7602 and L-7607. SILWET L-77 is an especially preferred ethoxylated wetting agent. It is believed to have Formula I above, where R and $R^3$ are —$CH_3$, $R^1$ is —$C_3H_6$—, $R^2$ is hydrogen, x is zero or one, y is one or two, a is about seven and b is zero.

An additional preferred class of organo-silicone wetting agents has the average formula

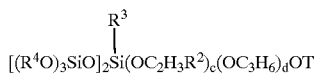

where $R^2$ and $R^3$ are defined above, each $R^4$ group is independently a monovalent hydrocarbyl radical with the proviso that at least a majority of the $R^4$ groups are sterically hindered alkyl radicals having at least three carbon atoms, c is at least four, d is greater than or equal to zero, with the further proviso that c has a sufficient value and d is small enough so that a composition of the invention has the desired dissolution rate of less than five minutes, and T is hydrogen, a monovalent alkyl or alkenyl radical, or a group of the formula —$Si(R^3)[OSi(OR^4)_3]_2$. Preferably in compounds of Formula III, $R^2$ is hydrogen, $R^3$ and T are —$CH_3$, $R^4$ is sec-butyl, c is five or more and d is zero. Representative ethoxylated wetting agents of Formula III are described in Olin Corp. product literature and in U.S. Pat. Nos. 4,160,776, 4,226,794, and 4,337,168, the disclosures of which are incorporated herein by reference.

An additional preferred class of organo-silicone wetting agents has the average formula

where $R^2$ and $R^4$ are as defined immediately above, e is at least four, f is greater than or equal to zero, with the further proviso that e has a sufficient value and f is small enough so that the composition of the invention has the desired dissolution rate of less than five minutes, and $T^1$ is hydrogen, a monovalent alkyl or alkenyl radical, or a group of the formula —$Si(OR^4)_3$. Preferably in compounds of Formula IV, $R^2$ is hydrogen, $R^4$ is sec-butyl, e is ten to 20, f is zero and $T^1$ is —$Si(sec\text{-}butoxy)_3$.

Suitable organosilicone wetting agents containing hydrocarbyl solubilizing groups are shown in "Surfactants and Detersive Systems", *Kirk-Othmer Encyclopedia of Chemical Technology*, 3rd Ed., 22, 360–377 (1983), the disclosure of which is incorporated herein by reference. Another preferred class of such organosilicone wetting agents has the average formula

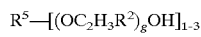

where $R^2$ is as defined above, $R^5$ is a saturated or unsaturated alkyl or alkylphenyl radical having at least seven carbon atoms, and g has a sufficient value so that the composition of the invention has the desired dissolution rate. Preferably, in compounds of Formula V, $R^5$ is alkyl and g is at least about five.

Fluoroorganic wetting agents useful in this invention are organic molecules containing at least about 30 percent by weight fluorine in the form of carbon-bonded fluorine in at least one fluoroaliphatic radical $R_f$ and at least one cationogenic group which is the radical of a base having an ionization constant (the logarithm of the reciprocal of said ionization constant being referred to as pKb) in water at 25° C. of at least about $10^{-6}$. Fluoroaliphatic wetting agents for use in this invention can also contain at least one anionogenic group which is the radical of an acid having an ionization constant (the logarithm of the reciprocal of said ionization constant being referred to as pKa) in water at 25° C. of at least about $10^{-6}$. Fluoroaliphatic wetting agents which contain the above-mentioned cationogenic groups but do not contain such anionogenic groups in the same molecule will be referred to herein as cationic fluoroaliphatic wetting agents. Fluoroaliphatic wetting agents will contain such cationogenic and such anionogenic groups in the same molecule will be referred to herein as amphoteric fluoroaliphatic wetting agents. Cationic, amphoteric, or mixtures of cationic and amphoteric fluoroaliphatic wetting agents can be used in this invention, with amphoteric fluoroaliphatic wetting agents and mixtures of cationic and amphoteric fluoroaliphatic wetting agents being preferred.

$R_f$ is a fluorinated, monovalent, aliphatic, preferably saturated organic radical containing at least 4 carbon atoms. The skeletal chain of $R_f$ can be straight, branched, or, if sufficiently large, cyclic, and can include divalent oxygen atoms or trivalent nitrogen atoms bonded only to carbon atoms. Preferably, $R_f$ is fully fluorinated, but hydrogen or chlorine atoms can be present as substituents on the skeletal chain, provided that not more than one atom of either hydrogen or chlorine is present for every two carbon atoms in the skeletal chain, and $R_f$ contains at least a terminal perfluoromethyl group. While radicals containing a large number of carbon atoms will function adequately, compounds containing not more than about 20 carbon atoms are preferred since larger radicals usually represent a less efficient utilization of fluorine than is possible with shorter skeletal chains. Preferably, $R_f$ contains about 5 to 14 carbon atoms.

The cationogenic groups in said cationic and said amphoteric fluoroaliphatic wetting agents are radicals of quaternary ammonium salts or radicals of cation-generating amines. Such amines can be oxygen-free (e.g., —$NH_2$) or oxygen-containing (e.g., amine oxides). Such cationogenic groups can have formulas such as —$NH_2$, —$(NH_3)X$, —$(NH(R^2)_2)X$, —$(N(R^2)_3)X$, or —$N(R^2)_2$→0 where X is a co-anion, such as halogen, hydroxide, sulfate, bisulfate or carboxylate, $R^2$ is H or $C_{1-8}$ and preferably $C_{1-6}$ alkyl, and each $R^2$ can be the same as or different from other $R^2$. Preferably $R^2$ is E or unsubstituted or substituted hydrocarbyl. Preferably, X is chloride, hydroxide, or bisulfate. Preferably, such wetting agents contain a cationogenic group which is a quaternary ammonium salt.

The anionogenic groups in said amphoteric fluoroaliphatic wetting agents are radicals of anions or are radicals which by ionization can become radicals of anions. The anionogenic groups can have formulas such as —COOM, —$SO_3M$, —$OSO_3M$, —$PO_3HM$, or —$OPO_3HM$, where M is H, a metal ion, or $N+(R^1)_4$ where each $R^1$ is independently H or substituted or unsubstituted $C_{1-6}$ alkyl. Preferably M is Na+ or K+. Preferably such anionogenic groups have the formulas —COOM, —$SO_3M$ or —$PO_3HM$.

Such cationic fluoroaliphatic wetting agents include those cationic fluorochemicals described, for example, in Guenthner and Vietor, *I & EC Product Res. & Dev.*, 1 (3) 165-9 (1962), and U.S. Pat. Nos. 2,732,398, 2,764,602, 2,764,603, 2,803,656, 2,809,990, 3,255,131, 4,000,168, 4,042,522, 4,069,158, 4,069,244, 4,090,967, 4,161,590, and 4,161,602.

Such amphoteric fluoroaliphatic wetting agents include those amphoteric fluorochemicals described, for example, in Guenthner and Vietor, id, Australian patent specification No. 432,809, and U.S. Pat. Nos. 2,764,602, 3,147,064, 3,450, 755, 4,042,522, 4,069,158, 4,090,967, 4,161,590, and 4,161, 602.

Representative fluoroaliphatic wetting agents containing the above-mentioned cationogenic groups (and the above-mentioned anionogenic groups, if such wetting agents are amphoteric) can be represented by several structural formulas, including formulas of nonionized (i.e., neutral) compounds and salts, including internal salts. Such representative wetting agents include those of Formula VI shown below (in the form of salts);

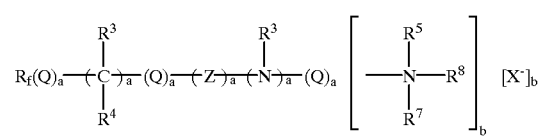

VI wherein: a is independently 0 or 1; b is 1 or 2; $R_f$ is a fluorinated, monovalent, aliphatic, preferably saturated organic radical containing at least 4 carbon atoms, with the proviso that the molecule contains at least about 30 weight percent fluorine in the form of carbon-bonded fluorine in $R_f$; Q is independently a polyvalent.

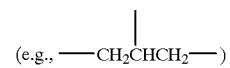

generally divalent (e.g., —$CH_2$—, —$C_2H_4$—, —$C_3H_6$—, —$C_6H_4$—, —$CH_2SCH_2$—, and —$CH_2OCH_2$—), hydrocarbylene linking group of 1 to 12 carbon atoms which can contain catenary oxygen or sulfur, is unsubstituted or substituted by halogen, hydroxyl, or aryl, and is preferably free of aliphatic unsaturation, with the proviso that at least one Q group is present in the molecule; $R^3$ is independently: $R^4$ wherein $R^4$ is H or alkyl which is unsubstituted or substituted with halogen, hydroxyl, or aryl and contains no more than a total number of 18 carbon atoms, with $R^4$ preferably being saturated, unsubstituted $C_{1-6}$ alkyl; $(Q)_a$ AM wherein A is —COO—, —$SO_3$—, —$OSO_3$—, —POSH—, or —$OPO_3H$—, and M is as defined above; or $QNR^5R^6R^7$ wherein $R^5$ and $R^6$ are independently H, substituted or unsubstituted alkyl of 1 to 18 carbon atoms (preferably 1 to 6 carbon atoms), or together with the N atom form a cyclic aliphatic or aromatic ring which can contain additional O, S, or N atoms, and $R^7$ is $R^4$, a quarternary ammonium group containing no more than 20 carbon atoms, or $(Q)_a$ AM; Z is —CO— or —$SO_2$—; and X is a coion such a halogen, hydroxide, sulfate, bisulfate or carboxylate.

Useful subgenera of Formula VI include compounds of the formula (shown as internal salts)

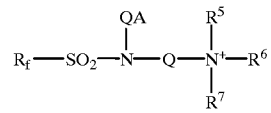

VII wherein $R_f$ contains 4 to 8 carbon atoms, Q is alkylene or hydroxyalkylene, A is —COO— or —$SO_3$— and $R^5$, $R^6$ and $R^7$ are alkyl or hydroxalkyl; and

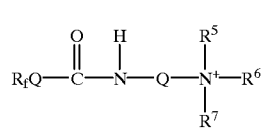

VIII wherein $R_f$ contains about 4 to 12 carbon atoms, Q is alkylene, $R^5$ and $R^6$ are lower alkyl and $R^7$ is carboxalkylene.

Representative cationic fluoroaliphatic wetting agents useful in this invention include those listed below. While particular structures are shown, in strongly acidic aqueous solution, such as electrowinning electrolyte, the cationogenic group of such structures will exist primarily in the protonated or salt form; and, in neutral or basic solution the cationogenic group of such structures tends to be in the form of the free base. Such solution-form structures are equivalents for purposes of the present invention.

$C_6F_{13}SO_2NHC_3H_6N(CH_3)_2$,
$[C_6F_{13}SO_2NHC_3H_6N(CH_3)_3]Cl^-$,
$C_6F_{13}SO_2NHC_3H_6N(CH_3)_2 \rightarrow O$,
$[C_6F_{13}SO_2NHC_3H_6N^+(CH_3)_2C_2H_4OH]OH^-$,
$C_6F_{13}SO_2N(C_2H_4OH)C_3H_6N(CH_3)2$,
$[C_6F_{13}SO_2N(C_2H_4OH)C_3H6N +(CH_3)_2C_2H_4OH]OH^-$,
$[C_6F_{13}C_2H_4SO_2NHC_3H_6N^+(CH_3)_3]OH^-$,
$[C_7F_{15}CONHC_3H_6N+(CH_3)_2H]C_1^-$,
$[C_8F_{17}SO_2NHC_3H_6N^+(CH_3)_3]I^-$,
$[C_8F_{17}SO_2NHC_3H_6N^+(CH_3)_3]_2SO_4^{2-}$,
$[C_8F_{17}SO_2NHC_3H_6N^+(CH_3)_3]O_3SOCH_3^-$,
$[C_8F_{17}C_2H_4N^+(CH_3)_2C_2H_4OH]OH^-$,
$[C_8F_{17}C_2H_4SC_2H_4CONHC_2H_4N^+(CH_3)_3]Cl^-$,

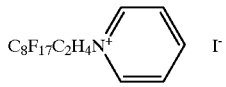

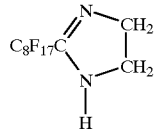

$C_{10}F_{19}OC_6H_4SO_2NHC_3H_6N(CH_3)_2$,
$(CF_3)_2CFOC_2F_4CONHC_3H_6N(CH_3)_2$, and mixtures thereof.

The cationic fluoroaliphatic wetting agents used in this invention can be prepared using methods known in the art, such as those described in the above references relating to cationic fluorochemicals.

Representative amphoteric fluoroaliphatic wetting agents useful in the practice of this invention are listed below. While particular structures are shown, in strongly acidic aqueous solution such as electrowinning electrolyte, the anionogenic group of such structures may be partly or completely protonated and the cationogenic group of such structures will exist primarily in the protonated or salt form, and, in neutral or basic solution the anionogenic group of such structures tends to be negatively ionized and the cationogenic group of such structures tends to be in the form of the free base; such solution-form structures are equivalents for purposes of the present invention. For example, a compound of the formula $R_fSO_2N(CH_2COONa)C_3H_6N(CH_3)_2$ will have the formula $R_fSO_2N(CH_2COOR)C_3H_6N^+H(CH_3)_2 \ HSO_4^-$ in aqueous sulfuric acid solution, and the formula $R_fSO_2N(CH_2COO-Na^+)C_3H_6N(CH_3)_2$ in aqueous sodium hydroxide solution.

$C_4F_9SO_2NHC_3H_6N^+(CH_3)_2CH_2COO^-$,
$C_4F_9CON(C_3H_6SO_3^-)C_3H_6N^+(CH_3)_2C_2H_4COOH$,
$C_6F_{13}C_2H_4SC_2H_4N^+(CH_3)_2CH_2COO^-$,
$C_6F_{13}SO_2NHC_3H_6N^+(CH_3)_2CH_2COO^-$,
$C_6F_{13}SO_2NHC_3H_6N^+(C_3)_2C_2H_4COO^-$,
$C_6F_{13}SO_2NHC_3H_6N^+(CH_3)_2C_3H_6SO_3^-$,
$[C_6F_{13}SO_2N(CH_2COONa)C_3H_6N^+(CH_3)_3]OH^-$,
$C_6F_{13}SO_2N(C_2H_4COONa)C_3H_6N^+(CH_3)_2C_2H_4COO^-$,

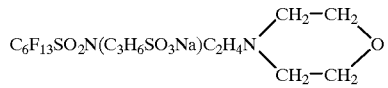

$C_6F_{13}SO_2N(C_3H_6SO_3Na)C_3H_6N(CH_3)_2$,
$C_6F_{13}SO_2N(C_3H_6SO_3^-)C_3H_6N^+(CH_3)_2C_2H_4OH$,
$C_6F_{13}SO_2N(CH_2CHOHCH_2SO_3Na)C_3H_6N(CH_3)_2$,
$C_6F_{13}SO_2N(CH_2CHOHCH_2SO_3^-)C_3H_6N^+(CH_3)_2C_2H_4OH$,
$[C_6F_{13}SO_2N(CH_2CHOHCH_2SO_3Na)C_3H_6N^+(CH_3)_2C_2H_4OH]OH^-$,
$C_6F_{13}C_2H_4SO_2N(CH_3)C_2H_4N^+(CH_3)_2C_2H_4COO^-$,
$C_7F_{15}CONHC_3H_6N^+(CH_3)_2C_2H_4COO^-$,
$C_7F_{15}CON(CH_2COO^-)C_3H_6N^+(CH_3)_3$,

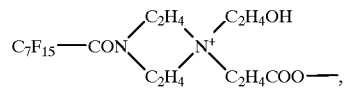

$C_7F_{15}C_2H_4SC_2H_4N^+(CH_3)_2CH_2COO^-$,
$C_8F_{17}CH_2CH(COO^-)N^+(CH_3)_3$,
$C_8F_{17}SO_2NHC_3H_6N^+(CH_3)_2C_3H_6SO_3^-$,
$C_8F_{17}SO_2N(C_2H_4PO_2OCH_3)^-C_3H_6N^+(CH_3)_3$,
$C_8F_{17}C_2H_4CONHC_3H_6N^+(CH_3)_2C_2H_4COO^-$,

$(CF_3)_2CFOC_3F_6CONHC_2H_4N^+(CH_3)_2C_2H_4COO^-$,
$C_{10}F_{19}OC_6H_4SO_2N(CH_2COONa)C_3H_6N(CH_3)_2$, and mixtures thereof.

The amphoteric fluoroaliphatic wetting agents used in this invention can be prepared using methods known in the art, such as those described in the above references relating to amphoteric fluorochemicals.

A preferred class of such nonionic wetting agents has the average formula

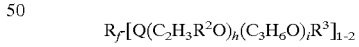

where $R^2$ is hydrogen or lower hydroxyalkyl radical and $R^3$ is hydrogen or a monovalent hydrocarbyl radical, $R_f$ is a fluorinated, monovalent or divalent, aliphatic, preferably saturated organic radical containing at least four carbon atoms and at least a terminal perfluoromethyl group, Q is a polyvalent (e.g., divalent) hydrocarbylene linking group (e.g., $-C_2H_4-$, or $-SO_2NR-$ where R is as defined above), h is greater than or equal to one, and i is greater than or equal to zero, with the proviso that h has a sufficient value and i is small enough so that the composition of the invention has the desired dissolution rate.

Preferred fluorochemical surfactants in the compositions of the present invention also include perfluoroalkyl sulfonyl compounds, perfluorocarboxyl compounds and perfluoroorganics including:

| TRADE DESIGNATION | CHEMICAL NAME OR STRUCTURE |
|---|---|
| EFTOP ® EF-112 | N-n-Propyl-N-perfluoro-octanesulfonyl-glycine K salt |
| EFTOP ® EF-121 | N-n-Propyl-N-perflouro-octanesulfonamide-ethanol |
| EFTOP ® EF-122C | Polyoxyethylene-N-n-perfluoro-octanesulfonamide-ethanol |
| EFTOP ® EF-123A | Di-(N-n-Propyl-N-perfluoro-octanesulfonamide-ethyl-phosphate |
| EFTOP ® EF-123B | Ammonium di(N-n-propyl-N-perfluoro-octane-sulfonamide-phosphate |
| EFTOP ® EF-132 | Perfluoro-octanesulfonamide-ethyl-trimethylamine-iodide |
| EFTOP ® EF-305 | Perfluoroalkyl alcohol |
| EFTOP ® EF-102 | $R_fSO_3K$ |
| EFTOP ® EF-103 | $R_fSO_3Na$ |
| EFTOP ® EF-104 | $R_fSO_3NH_4$ |
| EFTOP ® EF-105 | $R_fSO_3Li$ |
| EFTOP ® EF-122A | $R_fSO_2N(R)(C_2H_4O)_nH$ (n = 20; R = $C_3H_7$; and $R_f$ = perfluoroacetyl) |
| EFTOP ® EF-122B | $R_fSO_2N(R)(C_2H_4O)_nH$ (n = 10; R = $C_3H_7$; and $R_f$ = perfluoroacetyl) |
| EFTOP ® EF-122C | $R_fSO_2N(R)(C_2H_4O)_nH$ (n = 3; R = $C_3H_7$; and $R_f$ = perfluorooctyl) |
| EFTOP ® EF-124 | $R_fSO_2N(R)C_2H_4OSO_3H$ |
| EFTOP ® EF-126 | $R_fSO_2N(R)C_2H_4OCOC_2H_5$ |
| EFTOP ® EF-127 | $R_fSO_2N(R)CH_2COOC_2H_5$ |
| EFTOP ® EF-132 | $R_fSO_2N(H)C_3H_6N^+(CH_3)_3I^-$ |
| EFTOP ® EF-204 | $R_fCOONH_4$ |
| EFTOP ® EF-302 | $R_fSO_2N(C_2H_4OH)(CH_2)$ |
| EFTOP ® EF-700 | $R_fSO_2N(H)C_3HN+(CH_3)_2C_2H_4COO^-$ |
| EFTOP ® EF-305 | $R_f$—OH |

In the above listing of suitable fluoroalkyl surfactants $R_f$ refers to perfluoroalkyl ($C_1$–$C_{20}$) or fluoroalkyl ($C_1$–$C_{20}$). R may be hydrogen or lower alkyl ($C_1$–$C_6$). Certain of the fluoroalkyl chemicals may be available from the 3M Company.

Fluorochemical wetting agents of Asahi Glass Co., Ltd. are also usable in the present invention and include the following:

| TRADE DESIGNATION | IONIC NATURE | CHEMICAL NAME |
|---|---|---|
| S-111 | Anionic | Salt of perfluoroalkyl carboxylic acid |
| S-112 | Anionic | Perfluoroalkyl phosphate |
| S-113 | Anionic | Salt of perfluoroalkyl carboxylic acid |
| S-121 | Cationic | Perfluoroalkyltrimethyl ammonium salt |

-continued

| TRADE DESIGNATION | IONIC NATURE | CHEMICAL NAME |
| --- | --- | --- |
| S-131 | Amphoteric | Perfluoroalkyl betaine |
| S-141 | Amphoteric | — |
| S-141 | Nonionic | — |
| S-145 | Nonionic | Perfluoroalkyl EO adduct |

Fluorochemical wetting agents of Dainippon Ink & Chem. Inc. are also usable in the present invention. These include:

| TRADE DESIGNATION | CHEMICAL NAME |
| --- | --- |
| Megafac ® F-110 | Salt of perfluoroalkyl sulfonic acid ($C_8$) |
| Megafac ® F-113 | Salt of perfluoroalkyl sulfonic acid ($C_5$–$C_8$) |
| Megafac ® F-120 | Salt of perfluorocarboxylic acid |
| Megafac ® F-142D | Perfluoroalkyl ethyleneoxide adduct (EO = 10) |
| Megafac ® F-144D | Perfluoroalkyl ethyleneoxide adduct (EO = 20) |
| Megafac ® F-150 | Perfluoroalkyl trimethyl ammonium salt |
| Megafac ® F-160 | Salt of perfluoroalkyl aminosulfonic acid |
| Megafac ® F-171 | Perfluoroalkyl (hydrophilic group containing) oligomer |
| Megafac ® F-172 | Perfluoroalkyl (hydrophobic group containing) oligomer |
| Megafac ® F-173 | Perfluoroalkyl (hydrophobic group containing) oligomer |
| Megafac ® F-177 | Perfluoroalkyl (hydrophilic group containing) oligomer |
| Megafac ® F-183 | Perfluoroalkyl (hydrophilic group containing) urethane |
| Megafac ® F-184 | Perfluoroalkyl (hydrophobic group containing) urethane |
| Megafac ® F-191 | Perfluoroalkyl phosphoric acid ester |
| Megafac ® F-812 | Salt of perfluoroalkyl carboxylic acid (F-120) 15% solution |
| Megafac ® F-815 | Blended emulsifier of fluorochemical surfactant |
| Megafac ® F-824 | Blended emulsifier of fluorochemical surfactant |
| Megafac ® F-833 | Blended emulsifier of fluorochemical surfactant |
| Megafac ® F-851 | Blended emulsifier of fluorochemical |
| Megafac ® F-854 | Blended emulsifier of fluorochemical |
| Megafac ® F-855 | Blended emulsifier of fluorochemical |

The following fluorochemical wetting agents of the 3M Company are also usable in the present invention.

| TRADE DESIGNATION | CHEMICAL NAME |
| --- | --- |
| Fluorad FC-93 | Ammonium salt of perfluoroalkylsulfonic acid |
| Fluorad FC-95 | Potassium salt of perfluoroalkylsulfonic acid |
| Fluorad FC-98 | Potassium salt of perfluoroalkylsulfonic acid |
| Fluorad FC-129 | Potassium salt of perfluoroalkylcarboxylic acid |
| Fluorad FC-135 | Perfluoroalkyl ammonium salt |
| Fluorad FC-170C | Perfluoroalkyl polyoxyethyleneethanol |
| Fluorad FC-430 | Fluoroalkylester |
| Fluorad FC-431 | Fluoroalkylester |

Fluorochemical wetting agents of Daikin Ind. Ltd. are also useful in the present invention. These include:

| TRADE DESIGNATION | CHEMICAL NAME |
| --- | --- |
| UNIDYNE DS-101 | Salt of perfluoroalkyl carboxylic acid |
| UNIDYNE DS-102 | Salt of perfluoroalkyl carboxylic acid |
| UNIDYNE DS-202 | Perfluoroalkyl ammonium salt |
| UNIDYNE DS-301 | Perfluoroalkyl betaine |
| UNIDYNE DS-401 | Perfluoroalkyl betaine |
| UNIDYNE DS-451 | Perfluoroalkyl oligomer |
| UNIDYNE DS-403 | Perfluoroalkyl ethylene oxide adduct |

It may be preferred to include in the rapidly soluble or dispersible compositions of the present invention additionally one or more herbicides including, for example, 2,4-D (2,4-dichlorophenoxyacetic acid); endothal (7-oxabicyclo(2,2,1)heptane-2,3-dicarboxylic acid); mecoprop ([2-(2-methyl-4-chlorophenoxy)propionic acid]; picloram (4-amino-3,5,6-trichloropicolinic acid), 2,4,5-T (2,4,5-trichlorophenoxyacetic acid), benzac (2,3,6-trichlorobenzoic acid); dicamba (3,6-dichloro-o-anisic acid), MCPA (4-chloro-o-tolyloxyacetic acid); dalapon (2,2-dichloropropionic acid); dichlorprop (2-(2,4-dichlorophenoxy)propionic acid); MCPB (4-(4-chloro-o-tolyloxy)butyric acid; bialaphos (dl-homoalanin-4-yl-methylphosphinate); glufosinate (ammonium (3-amino-3-carboxypropyl)-methylphosphinate; Pursuit (2-[4,5-dihydro-4-methyl-4-(1-methylethyl)-5-oxo-1H-imidazol-2-yl]-5-ethyl-3-pyridine carboxylic acid); Scepter (2-[4,5-dihydro-4-methyl-4-(1-methylethyl)-5-oxo-1H-imidazol-2-yl]-3-quinolinecarboxylic acid); mixtures thereof and the like.

It may be preferred to utilize a solid, water insoluble co-herbicide. In such embodiment, the co-herbicide is present in the composition as a fine powder. Illustrative coherbicides include sulfonyl-ureas such as Oust (2-[3-(4,6-dimethylpyrimidin-2-yl)ureidosulphonyl]benzoic acid); Glean (1-(2-chloro-phenylsulphonyl)-3-(4-methoxy-6-methyl-1,3,5-triazin-2-yl)urea)]; Ally (methyl 2-[[[[4-methoxy-4-methyl-1, 3,5-triazin-2-yl)amino]carbonyl]-amino]sulfonyl]-benzoate); Classic (ethyl 2-[(4-chloro-6-methoxy-pyrimidin-2-yl) amino]-carbonyl]amino] sulfonyl]-benzoate); diuron (3-(3,4-dichlorophenyl)-1,2-dimethylurea); linuron (3-(3,4-dichlorophenyl)-1-methoxy-1-methylurea); atrazine (2-chloro-4-(ethyl-amino)-6-(isopropylamino)-s-triazine; simazine (2-chloro-4,6-bis (ethylamino)-S-triazine), mixtures thereof and the like.

The water insoluble co-herbicide may be liquid or solid present in said composition as a water dispersible granule such as atrazine; fomesafen (5-[2-chloro-4-(trifluoromethyl)-phenoxy]-N-methyl-sulfonyl)-2-nitrobenzamide); oxyfluorfen (2-chloro-1-(3-ethoxy-4-nitrophenoxy)-4-(trifluoromethyl)benzene); feroe ([fenoxaprop-ethyl:(±)-ethyl-2,4-(6-chloro-2-benzoxazolyl) oxy+phenoxy]propanoate); simazine; diuron; Ally; Classic; linuron; Oust; Glean mixtures thereof and the like.

The glyphosate salt component of a compositions of this invention may be preferably prepared by admixing various bases (acid acceptors) including those selected from those listed below with glyphosate wet cake or moistened glyphosate. Ammonium hydroxide, ammonium and alkali metal carbonates, bicarbonates, meta borates, citrates, formates, oxalates, phosphates, propionates, pyrophosphates, metasilicates, orthosilicates, sulfites, thiosulfates, tetraborate, monoacid phosphates, tripolyphosphates, metaphosphates, sodium hydroxide, potassium hydroxide, tetrasodium EDTA, mixtures thereof and the like. Mixtures of glyphosate and salts thereof may be employed as starting materials.

As employed herein, the term "admixed" includes reaction, neutralization and partial neutralization of glyphosate as well as mixed with and sprayed on, combined with or added to at least one other ingredient.

Suitable additional or secondary wetting agents include nonionic surfactants, anionic surfactants, cationic surfactants and amphoteric surfactants, mixtures thereof and the like, preferably those surfactants that provide increased herbicidal activity of N-phosphonomethylglycine. A most preferred surfactant is an ethoxylated tallow amine containing 15–18 moles of ethylene oxide.

Examples of nonionic secondary wetting agents to be used together with the organosilicone block copolymer or the fluorinated compound as the primary wetting agent are polyoxyethylene alkyether, polyoxyethylene alkylarylether, polyoxyalkylene alkyl arylether formaldehyde condensates, polyoxyethylene-alkylene arylether, polyoxyalkylene alkylester, polyoxyalkylene alkyl sorbitan ester, polyoxyalkylene alkyl sorbitol ester, polyoxyalkylene alkyl glycerol ester, polyoxyalkylene block copolymer, polyoxyalkylene block copolymer alkyl glycerol ester, polyoxyalkylene alkyl sulfonamides, polyoxyalkylene rosin ester, polyoxypropylene block copolymers, polyoxyethylene oleyl ether, polyoxyalkylene alkylphenol, mixtures thereof and the like.

Examples of secondary liquid cationic wetting agents are polyoxyalkylene alkylamines such as ethoxylated tallow amine, ethoxylated oleylamine, ethoxylated soyamine, ethoxylated cocoamine, ethoxylated synthetic alkyl amines, ethoxylated III° octyl amine, etc. and mixtures thereof.

Examples of secondary anionic wetting agents (typically solids unless dissolved in water) are sodium alkyl sulfate, sodium mono- and di-alkyl naphthalene sulfonates, sodium alpha-olefin sulfonate, sodium alkane sulfonates, alkylsulfates, polyoxyalkyene alkylether sulfate, polyoxyalkylene alkyl-arylether sulfates, polyoxyalkylene styrylphenylether sulfate, mono- and di-alkylbenzene sulfonates, alkylnaphthalene sulfonate, alkylnaphthalene sulfonate formaldehyde condensate, alkyl diphenylether sulfonates, olefinic sulfonates, alkylphosphates, polyoxyalkylene alkyl phosphates, polyoxyalkylene phenylether phosphate, polyoxyalkylphenol phosphates, polycarboxylates, fatty acids salts, stearic acid and salts thereof, oleic acid and salts thereof, N-methyl fatty acid taurides, mixtures thereof and the like, including sodium, potassium, ammonium and amine salts.

Examples of suitable secondary amphoteric wetting agents are lauryldimethylamine oxide, Armox C/12, amine oxides, Monaterics, Miranols, betaines, Lonzaines, other amine oxides, mixtures thereof and the like.

Preferable agriculturally acceptable salts of N-phosphonomethylglycine include the ammonium, isopropylamine, trimethylsulfonium, imminourea salts, sodium, potassium, mixtures thereof and the like. The sodium potassium and ammonium salts of N-phosphonomethylglycine are especially preferred in this invention. Mixtures of water soluble salts of N-phosphonomethylglycine may be employed herein, as well as surfactant salts of N-phosphonomethylglycine including, for example, a N,N-bis(hydroxyethylcocoamine) salt of N-phosphonomethylglycine, Most preferred water-soluble granules (WSG) are those made with the ammonium salt or sodium salt of N-phosphonomethylglycine and an ethoxylated tallowamine surfactant (tallowamine+15–20 moles of ethylene oxide) as the surfactant.

In another embodiment the composition of this invention further comprises ammonium sulfate, potassium sulfate, potassium chloride, sodium sulfate, urea, ammonium phosphate mixtures thereof and the like.

If desired, a dry, water soluble, agriculturally acceptable composition comprising a water soluble, agriculturally acceptable salt of N-phosphonomethylglycine may be prepared by pan granulation or extrusion granulation of the salt of glyphosate itself. If pan granulation is to be employed, an intermediate drying step after preparing the salt may be necessary before pan granulation is carried out.

The salt of N-phosphonomethylglycine may be prepared by admixing an acid acceptor with N-phosphonomethylglycine (containing in the range from about 10 to about 15 wt % water) to neutralize the N-phosphonomethylglycine. A slight excess of acid acceptor may be preferred, however it is not required when ammonia, ammonium, hydroxide or ammonium bicarbonate is the base.

When the composition of this invention comprises a water soluble salt of N-phosphonomethylglycine, the process of preparation comprises preparing said water soluble salt of N-phosphonomethylglycine followed by granulation (pan, extrusion, fluidized bed, or equivalent such as spray drying, drum drying, flaking, crystallizing and centrifuging) to form a composition of this invention.

In this embodiment, water is added in a pan granulation step to promote granulation and is thereafter removed in subsequent drying. If extrusion granulation is employed then a water removal step is usually but not always necessary.

A fluidized bed drying step is usually carried out following granulation to form a composition of this invention. Reworking of the granules may be necessary at times to take into account various parameters such as temperature, ingredient quality, and the like.

When the composition of this invention includes a liquid wetting agent the process of preparation comprises admixing said water soluble, agriculturally acceptable salt of N-phosphonomethylglycine and said one or more liquid wetting agents optionally with ammonium sulfate and thereafter blending these ingredients singly or collectively to form an admixed composition as a composition of this invention.

The wetting agent or mixture of wetting agent may be admixed with the water soluble salt of N-phosphonomethylglycine by spraying the wetting agent on the water soluble salt of N-phosphonomethylglycine while the water soluble salt of N-phosphonomethyl-glycine is being pan granulated to form a composition of this invention. The one or more liquid wetting agent may be admixed with the water soluble salt of N-phosphonomethylglycine as in a blender prior to granulation. In the latter embodiment, water is typically added to the granulator to promote granulation in forming a composition of this invention.

If desired, in another embodiment water may be sprayed onto the admixed composition comprising water soluble salt of N-phosphonomethylglycine and optionally wetting agent while said admixed composition is being pan granulated to form a composition of this invention.

Typically the admixed composition will have an appearance (depending on the amount of water present at that time) which ranges from a damp or moist powder, even fluffy, to that of a dough like substance after the admixing is completed in a kneader, blender or other mixer type device. Thereafter, additional water present in the mixed composition may be removed to a satisfactory level for granulation (pan, extrusion, fluid bed or equivalent) which may in turn be followed by fluidized bed drying. Carbon dioxide and water may be removed in the drying process.

If extrusion granulation is desired, an admixed composition may be fed to an extruder without an intermediate drying and thereafter the extrusion product, the extruded admixed composition, may be further dried in a fluidized bed dryer or other drying equipment (drying oven, flash or vacuum dryer, etc.) to form a composition of this invention.

This invention also includes a method of killing or controlling weeds by applying a herbicidally effective amount of the composition of this invention to the locus of the plant or weed to be killed or controlled. Dilution with water before application to the locus of the plant or weed is desirable, although perhaps not necessary in all cases, as for example when the plants contain dew. In general when killing or controlling weeds or plants using this invention, the methods of use generally disclosed in U.S. Pat. No. 3,799,458 for salts and compositions employing N-phosphonomethylglycine and the other patents referred to hereinabove will be useful to those of skill in the art.

The application of an effective amount of the herbicidally effective compounds used in the compositions of this invention to the plant is essential for the practice of the present invention. The exact amount of herbicide containing N-phosphonomethylglycine as the active ingredient to be employed is dependent upon the response desired in the plant, as well as such other factors as the plant species and stage of development thereof, and the amount of rainfall, as well as the specific salt employed. In foliar treatment for the control of vegetative growth, the active ingredients are applied in amounts from about 0.01 to about 20 or more pounds per acre. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e. a phytotoxic or herbicidal amount. It is believed that one skilled in the art can readily determine from the teachings of this specification, and patents referred herein the approximate application rate. Granules may also be applied using conventional broadcast techniques.

The following examples are presented to illustrate the present invention, as well as some of the various embodiments of the invention. These examples are presented as being illustrative of the novel formulations, process for preparing the invention and and herbicidal use thereof and are not intended to be a limitation of the scope of this invention. All percentages in the following examples are on a weight basis unless otherwise indicated.

GENERAL ADMIXING PROCESS

In a typical process for preparing the ammonium salt water soluble granules (or other water soluble salts of N-phosphonomethylglycine) of this invention, the process comprises first neutralizing N-phosphonomethylglycine wet cake (contains about 1 to about 15% water) with ammonium bicarbonate (or sodium carbonate or sodium bicarbonate) by admixing process in a mixer such as a ribbon blender or a Hobart type mixer to form a suitable water soluble salt of N-phosphonomethylglycine (e.g., ammonium or sodium salt).

The products of the reaction include the ammonium salt of N-phosphonomethylglycine, carbon dioxide and water. As the reaction proceeds there is a loss in weight of the formulation. If desired, the reaction can be monitored by the rate of carbon dioxide formation and consequential weight loss. The time involved for the reaction to proceed to completion may range from about twenty to thirty minutes to about one hour. The optimum particle size is about 20 mesh for the admixed composition.

After the N-phosphonomethylglycine-ammonium bicarbonate reaction has been completed, a fluffy wet cake or white powder of ammonium salt of N-phosphonomethylglycine has formed. At the time, the ammonium salt of N-phosphonomethylglycine can either be subsequently formulated into a water soluble granule to form a composition of this invention or dried, or used as is for some other use such as in package mixes to also form a composition of this invention.

Wetting Agent Addition and Mixing

After making the salt of N-phosphonomethyl-glycine as described just above, one optionally adds at least one surfactant. The preferred surfactant is an ethoxylated fatty tallow amine with an average ethylene oxide content of about 15–18 moles (MON-0818). The addition of a surfactant typically produces a stiff dough. The mixing equipment is appropriately selected to be capable of mixing such a dough; and the equipment should also be steam jacketed to allow heating of the contents to drive off excess water to form a damp powder in the event pan granulation is to follow as a further processing step. Depending on the amount of water present, the admixed composition at this step may be a composition of this invention.

Pan Granulation

If desired, the moist but free flowing mixture of active and surfactant is fed into a typical pan granulator and granulated to form a composition of this invention. Water may be added in the granulation step. In order to achieve the most desired granule characteristics, it may be desirable to experiment with the granulator's operating characteristics.

Another approach is to granulate the water soluble salt of N-phosphonomethylglycine in a piece of equipment known as a turbulator which is basically a modified pug mixer that mixes thoroughly. The powder is added at one end. Liquid is sprayed on during mixing which forms granules that come out the other end and are ready for drying. This approach could be used in place of the surfactant addition and mixing step to combine the mixing step with the granulating step. Other suitable methods of granulating include the use of fluid bed granulation, tumble granulation techniques, or granulating using Schugi granulation equipment.

METHODS OF GRANULATION

A number of different methods may be used to make WSG. Some WSG may be made by spraying a liquid wetting agent directly on the active-containing powder in a pan granulator (or disk pelletizer). The wetting agent can be mixed with the active-containing powder in a blender and this mixture granulated by spraying water onto the powder. Little difference in the granule quality was noted. Other equipment suitable for making the granules include: Patterson-Kelley V-blenders, extruders, ribbon blenders, and fluid beds.

Extrusion Granulation

If desired, one may proceed from the first step to extrusion granulation. In such embodiment, the product from the admixing device is fed to an extruder and the extruded product of this invention is typically a cylindrical shaped particle, typically having a diameter in the range from about 0.4 to about 2.0 mm and preferably in the range from about 0.7 to 1.2 mm and having a length in the range from about 1 to 10 mm and preferably from about 2 mm. to about 5 mm.

After granulation, further drying of the composition is typically desired to form a composition of this invention.

METHODS OF DRYING

A preferred method of drying is the use of a fluid bed drier which allows drying to occur quickly under more temperate conditions than other methods. For small size samples, drying can be accomplished at a 60° C. to 70° C. in a few hours or in an oven overnight.

The water content of the active salt powder was also found to have an effect on the size granules formed in a pan granulator and on the quality of the WSG. The active-containing powder can be a free flowing powder while containing as much as about 18–20% water. It was found that a minimum water content of about 5–7% was needed to form granules of good quality. About 10 to 15% were found to be the optimum water content. When the water content was below about 5–7% for pan granulation, the sodium and ammonium active salt granules may be noticeably soft and powdery on the inside.

Water may be added in the active-containing powder to be granulated or, if desired, the wetting agent can be mixed with water that is sprayed on the powder. Even when the water was contained in the wetting agent, an optimum water content for granulation was one in which the total amount of water amounted to approximately 10% of the weight of the active.

A minimum water content was found to be necessary even when the process to make the granules was changed such that the wetting agent was blended in a mixer with the active-containing powder and the resultant powder granulated. When "bone dry" ammonium salt of N-phosphonomethylglycine was mixed with Sterox NJ (nonylphenol+9.5 moles EO) and the resulting powder granulated, the granules were soft. When the ammonium salt contained about 10% water when the surfactant was mixed in, the granules formed were of very good quality.

It is advantageous that water be present while the granules are forming. Once the granules are formed, excess water can be removed by drying and the granules will be high quality, sturdy granules.

The water can be removed either in an oven or fluid bed drier.

The following examples were prepared in general accordance with the above general procedures although departures were employed to adjust for batch size and general equipment availability. The identity and quantity of ingredients are provided for each composition.

In the examples, particles of a water soluble salt of N-phosphonomethylglycine and organosilicone and/or fluorocarbon wetting agents were prepared as follows.

Selected quantities of the water soluble salt of N-phosphonomethylglycine, and optional ingredients, such as ammonium sulfate and a secondary wetting agent, were ground and mixed using a mortar and pestle. After thorough mixing, selected quantities of the organosilicone or fluoroorganic compound were added and mixed with the mixture for about thirty (30) minutes. The resulting mixture was a solid powder.

To the powder selected quantities of water were kneaded at room temperature for fifteen (15) minutes. The kneaded product was a dough-like material. The dough was then fed into an extruder and through holes of 1.0 mm diameter. The extrudate was cut into rods having a diameter of 1.0 mm and lengths of 1–5 mm. The average length was 3 mm. The rods were dried in an electrical oven equipped with a fan for 1–2 hours at 60–70° C. The dried rods were screen by a sifter to 12/48 mesh.

To test the time of dissolution one gram of the shaped solid rods was placed in 100 ml of 3° hard water at 20° C. contained in a 100 ml graduated cylinder. The cylinder was stopped and gently rotated in one direction from being right side up to down side up. The rotation was continued until the shaped rods were completely dissolved or completely dispersed in the water. The time taken to obtain complete dissolution was noted. In the following tables test data of various compositions of the present invention are provided showing the time of dissolution versus the same composition to which no silicone copolymer wetting agent or fluoroorganic wetting agent had been added.

In the examples the term "ae" means acid equivalent. The term "ai" means active ingredient. The Dissolution Rate in the tables is the time given in minutes required to dissolve or disperse a one gram sample in 100 ml 30 hard water at 20° C. in a stoppered 100 ml graduate cylinder by rotating the cylinder and contents around its short axis at a rate of about one rotation every two seconds.

EXAMPLE 1

21 g of the ammonium salt of glyphosate, 71 g of ammonium sulfate and 5 g of Sorpol 7553 (surfactant) were mixed with a pestle in a mortar; and then 2 g of silicone surfactant was added and mixed for about 30 minutes.

The resultant mixture was solid powder. About 6 g of water was added to the admixture and the mixture was kneaded at room temperature for 15 minutes. The resultant mixture is dough like material. The dough was then fed into the extruder and was extruded through holes of 1.0 mm diameter. The extruded granules (diameter 1.0 mm, length 1–5 mm) were dried in a fan electrical oven for 1–2 hours at 60–70° C. The dried granules were screened by a sifter to 12/48 mesh. The results using the tested silicone copolymer wetting agents are set forth in Tables 1–2. The results using the tested fluorochemical wetting agents are set forth in Table 3. The term "WSG" refers to water soluble granules.

TABLE 1

Effect of Silicone Wetting Agents on Dissolution of WSG of Glyphosate

| Ingredients | 1-1 | 1-2 | 1-3 | 1-4 | 1-5 | 1-6 | 1-7 | 1-8 | 1-9 | Control |
|---|---|---|---|---|---|---|---|---|---|---|
| MON-8750 (88% ae) | 21.0 | 21.0 | 21.0 | 21.0 | 21.0 | 21.0 | 21.0 | 21.0 | 21.0 | 21.0 |
| Sorpol 7553 | 6.0 | 6.0 | 6.0 | 6.0 | 6.0 | 6.0 | 6.0 | 6.0 | 6.0 | 6.0 |
| Ammonium sulfate | 71.0 | 71.0 | 71.0 | 71.0 | 71.0 | 71.0 | 71.0 | 71.0 | 71.0 | 73.0 |
| Silwet FZ-2104 | 2.0 | — | — | — | — | — | — | — | — | — |
| Silwet L-5310 | — | 2.0 | — | — | — | — | — | — | — | — |
| Silwet L-7001 | — | — | 2.0 | — | — | — | — | — | — | — |
| Silwet L-7600 | — | — | — | 2.0 | — | — | — | — | — | — |

TABLE 1-continued

Effect of Silicone Wetting Agents on Dissolution of WSG of Glyphosate

| | Example No. | | | | | | | | | |
|---|---|---|---|---|---|---|---|---|---|---|
| Ingredients | 1-1 | 1-2 | 1-3 | 1-4 | 1-5 | 1-6 | 1-7 | 1-8 | 1-9 | Control |
| Silwet L-7604 | — | — | — | — | 2.0 | — | — | — | — | — |
| Silwet L-7607 | — | — | — | — | — | 2.0 | — | — | — | — |
| Silwet F-218-02 | — | — | — | — | — | — | 2.0 | — | — | — |
| Silwet F-218-05 | — | — | — | — | — | — | — | 2.0 | — | — |
| Silwet F-218-06 | — | — | — | — | — | — | — | — | 2.0 | — |
| Total, w/w, % | 100.0 | 100.0 | 100.0 | 100.0 | 100.0 | 100.0 | 100.0 | 100.0 | 100.0 | 100.0 |
| Water for Kneading | 6.0 | 6.0 | 6.0 | 6.0 | 6.0 | 6.0 | 6.0 | 6.0 | 6.0 | 6.0 |
| Dissolution Rate | 3.0 | 2.0 | 1.5 | 1.0 | 2.0 | 0.5 | 0.5 | 1.0 | 0.5 | 8.0 |

MON-8750 is the monoammonium salt of glyphosate.
Sorpol 7553 is ethoxylated alkylamine obtained from Toho.

TABLE 2

Effect of Silicone Wetting Agents on Dissolution of WSG of Glyphosate

| | Example No. | | |
|---|---|---|---|
| Ingredients | 1-10 | 1-11 | Control |
| MON-8750 (88% ae) | 21.0 | 21.0 | 21.0 |
| Sorpol 7553 | 6.0 | 6.0 | 6.0 |
| Ammonuim sulfate | 71.0 | 71.0 | 73.0 |
| Silwet F-218-06A | 2.0 | — | — |
| F-218-10 | — | 2.0 | — |
| Total, w/w, % | 100.00 | 100.00 | 100.00 |
| Water for Kneading | 6.0 | 6.0 | 6.0 |
| Dissolution Rate | 0.5 | 0.5 | 8.0 |

EXAMPLE 2

21 g of MON 8750 (the monoammonium salt of glyphosate), 72 g of ammonium sulfate Powder and 6 g of Sorpol 7553 (surfactant) were mixed with a pestle in a mortar; and then 1 g of fluorochemical wetting agent was added and mixed with a pestle for about 30 minutes.

The resultant mixture is solid powder. About 6 g of water was added to the admixture and the same was kneaded at room temperature for 15 minutes. The resultant mixture was a dough like material. The dough was then fed into the extruder and was extruded through holes of 1.0 mm diameter. The extruded granules (diameter 1.0 mm, length 1–5 mm) were dried in a fan electrical oven for 1–2 hrs at 60–70° C. The dried granules were screened by a sifter to 12/48 mesh. The results using the tested fluorochemical wetting agents are given in Tables 4–6.

TABLE 3

Effect of Fluorochemical Wetting Agents on Dissolution of WSG of Glyphosate

| | Example No. | | | | | | | | | |
|---|---|---|---|---|---|---|---|---|---|---|
| Ingredients | 1-12 | 1-13 | 1-14 | 1-15 | 1-16 | 1-17 | 1-18 | 1-19 | 1-20 | Control |
| MON-8750 (88% ae) | 21.0 | 21.0 | 21.0 | 21.0 | 21.0 | 21.0 | 21.0 | 21.0 | 21.0 | 21.0 |
| Sorpol 7553 | 6.0 | 6.0 | 6.0 | 6.0 | 6.0 | 6.0 | 6.0 | 6.0 | 6.0 | 6.0 |
| Ammonium sulfate | 72.0 | 72.0 | 72.0 | 72.0 | 72.0 | 72.0 | 72.0 | 72.0 | 72.0 | 73.0 |
| Megafac F-110 (100% ai) | 1.0 | — | — | — | — | — | — | — | — | — |
| Megafac F-120 (100% ai) | — | 1.0 | — | — | — | — | — | — | — | — |
| Megafac F-142D (100% ai) | — | — | 1.0 | — | — | — | — | — | — | — |
| Megafac F-150 (100% ai) | — | — | — | 1.0 | — | — | — | — | — | — |
| Megafac F-177 (100% ai) | — | — | — | — | 1.0 | — | — | — | — | — |
| Megafac F-191 (100% ai) | — | — | — | — | — | 1.0 | — | — | — | — |
| Eftop EF-112 | — | — | — | — | — | — | 1.0 | — | — | — |
| Eftop EF-121 | — | — | — | — | — | — | — | 1.0 | — | — |
| Eftop EF-123A | — | — | — | — | — | — | — | — | 1.0 | — |
| Total, w/w, % | 100.0 | 100.0 | 100.0 | 100.0 | 100.0 | 100.0 | 100.0 | 100.0 | 100.0 | 100.0 |
| Water for Kneading | 7.0 | 6.0 | 6.0 | 7.0 | 7.0 | 6.0 | 6.0 | 6.0 | 6.0 | 6.0 |
| Dissolution Rate | 3.0 | 1.0 | 1.5 | 3.0 | 3.0 | 1.5 | 1.5 | 1.5 | 2.5 | 8.0 |

TABLE 4

Effect of Fluorochemical Wetting Agents on Dissolution of WSG of Glyphosate

| Ingredients | 2-1 | 2-2 | 2-3 | 2-4 | 2-5 | 2-6 | 2-7 | 2-8 | 2-9 | Control |
|---|---|---|---|---|---|---|---|---|---|---|
| MON-8750 (88% ae) | 21.0 | 21.0 | 21.0 | 21.0 | 21.0 | 21.0 | 21.0 | 21.0 | 21.0 | 21.0 |
| Sorpol 7553 | 6.0 | 6.0 | 6.0 | 6.0 | 6.0 | 6.0 | 6.0 | 6.0 | 6.0 | 6.0 |
| Ammonium sulfate | 72.0 | 72.0 | 72.0 | 72.0 | 72.0 | 72.0 | 72.0 | 72.0 | 72.0 | 73.0 |
| ETOP ® EF-123B | 1.0 | — | — | — | — | — | — | — | — | — |
| ETOP ® EF-132 | — | 1.0 | — | — | — | — | — | — | — | — |
| ETOP ® EF-305 | — | — | 1.0 | — | — | — | — | — | — | — |
| Fluorad FC-95 (100% ai) | — | — | — | 1.0 | — | — | — | — | — | — |
| Fluorad FC-98 (100% ai) | — | — | — | — | 1.0 | — | — | — | — | — |
| Fluorad FC-129 (50% ai) | — | — | — | — | — | 1.0 | — | — | — | — |
| Fluorad FC-135 (50% ai) | — | — | — | — | — | — | 1.0 | — | — | — |
| Fluorad FC-170C (95% ai) | — | — | — | — | — | — | — | 1.0 | — | — |
| Fluorad FC-430 (100% ai) | — | — | — | — | — | — | — | — | 1.0 | — |
| Total, w/w, % | 100.0 | 100.0 | 100.0 | 100.0 | 100.0 | 100.0 | 100.0 | 100.0 | 100.0 | 100.0 |
| Water for Kneading | 6.0 | 6.0 | 6.0 | 6.0 | 6.0 | 6.0 | 6.0 | 6.0 | 6.0 | 6.0 |
| Dissolution Rate | 1.0 | 3.0 | 0.5 | 3.0 | 2.5 | 0.5 | 1.5 | 1.0 | 0.5 | 8.0 |

TABLE 5

Effect of Fluorochemical Wetting Agents on Dissolution of WSG of Glyphosate

| Ingredients | 2-10 | 2-11 | 2-12 | 2-13 | 2-14 | 2-15 | 2-16 | 2-17 | 2-18 | Control |
|---|---|---|---|---|---|---|---|---|---|---|
| MON-8750 (88% ae) | 21.0 | 21.0 | 21.0 | 21.0 | 21.0 | 21.0 | 21.0 | 21.0 | 21.0 | 21.0 |
| Sorpol 7553 | 6.0 | 6.0 | 6.0 | 6.0 | 6.0 | 6.0 | 6.0 | 6.0 | 6.0 | 6.0 |
| Ammonium sulfate | 72.0 | 72.0 | 72.0 | 72.0 | 72.0 | 72.0 | 72.0 | 72.0 | 72.0 | 73.0 |
| Surflon S-111 (30% ai) | 1.0 | — | — | — | — | — | — | — | — | — |
| Surflon S-112 (15% ai) | — | 1.0 | — | — | — | — | — | — | — | — |
| Surflon S-113 (30% ai) | — | — | 1.0 | — | — | — | — | — | — | — |
| Surflon S-121 (30% ai) | — | — | — | 1.0 | — | — | — | — | — | — |
| Surflon S-131 (30% ai) | — | — | — | — | 1.0 | — | — | — | — | — |
| Surflon S-132 (30% ai) | — | — | — | — | — | 1.0 | — | — | — | — |
| Surflon S-141 (30% ai) | — | — | — | — | — | — | 1.0 | — | — | — |
| Surflon S-145 (30% ai) | — | — | — | — | — | — | — | 1.0 | — | — |
| Unidyne DS-102 (100% ai) | — | — | — | — | — | — | — | — | 1.0 | — |
| Total, w/w, % | 100.0 | 100.0 | 100.0 | 100.0 | 100.0 | 100.0 | 100.0 | 100.0 | 100.0 | 100.0 |
| Water for Kneading | 6.0 | 6.0 | 6.0 | 6.0 | 6.0 | 6.0 | 6.0 | 6.0 | 6.0 | 6.0 |
| Dissolution Rate | 2.5 | 2.0 | 1.5 | 2.0 | 2.5 | 0.5 | 2.0 | 2.0 | 5.0 | 8.0 |

TABLE 6

Effect of Fluorochemical Wetting Agents on Dissolution of WSG of Glyphosate

| Ingredients | 2-19 | 2-20 | 2-21 | Control |
|---|---|---|---|---|
| MON-8750 (86% ae) | 21.0 | 21.0 | 21.0 | 21.0 |
| Sorpol 7553 | 6.0 | 6.0 | 6.0 | 6.0 |
| Ammonium sulfate | 72.0 | 72.0 | 72.0 | 73.0 |
| Unidyne DS-202 | 1.0 | — | — | — |
| Unidyne DS-401 | — | 1.0 | — | — |
| Unidyne DS-403 | — | — | 1.0 | — |
| Total, w/w, % | 100.0 | 100.0 | 100.0 | 100.00 |
| Water for Kneading | 6.0 | 6.0 | 6.0 | |
| Dissolution Rate | 1.5 | 1.5 | 1.5 | 8.0 |

EXAMPLE 3

Ninety six (96) grams of the monoammonium salt of glyphosate and 2 grams of tallowamine ethoxylated (20 moles EO per mole of amine) as a surfactant were mixed with a pestle in a mortar. After thorough mixing of the salt and amine, two (2) grams of the tested organosilicone or fluorochemical (as a water dissolution enhancing aid) was added and mixed with the mixture of salt and amine for about thirty (30) minutes. The resulting mixture was a solid powder.

To the powder six (6) grams of water were kneaded at room temperature for fifteen (15) minutes. The kneaded product was a dough like material. The dough was then fed into an extruder and through holes of 1.0 mm diameter. The extrudate was cut into rods having lengths of 1–5 mm. The rods were dried in an electrical oven equipped with a fan for 1–2 hours at 60–70° C. The dried rods were screened by a sifter to 12/48 mesh. The results of the tested organosilicone and fluorochemical wetting agents are given in Tables 7–13.

TABLE 7

Effect of Silicone Wetting Agents on Dissolution of WSG of Glyphosate

| | Example No. | | | | | | | | |
|---|---|---|---|---|---|---|---|---|---|
| Ingredients | 3-1 | 3-2 | 3-3 | 3-4 | 3-5 | 3-6 | 3-7 | 3-8 | Control |
| MON-8750 (88% ae) | 96.0 | 96.0 | 96.0 | 96.0 | 96.0 | 96.0 | 96.0 | 96.0 | 98.0 |
| Sorpol 7553 | 2.0 | 2.0 | 2.0 | 2.0 | 2.0 | 2.0 | 2.0 | 2.0 | 2.0 |
| Silwet L-7600 (100% ai) | 2.0 | — | — | — | — | — | — | — | — |
| Silwet L-7001 (100% ai) | — | 2.0 | — | — | — | — | — | — | — |
| Silwet L-5310 (100% ai) | — | — | 2.0 | — | — | — | — | — | — |
| Silwet L-7604 (100% ai) | — | — | — | 2.0 | — | — | — | — | — |
| Silwet F-218-05 (100% ai) | — | — | — | — | 2.0 | — | — | — | — |
| Silwet F-218-06 (100% ai) | — | — | — | — | — | 2.0 | — | — | — |
| Silwet F-218-10 (100% ai) | — | — | — | — | — | — | 2.0 | — | — |
| Silwet F-218-02 (100% ai) | — | — | — | — | — | — | — | 2.0 | — |
| Total, w/w, % | 100.0 | 100.0 | 100.0 | 100.0 | 100.0 | 100.0 | 100.0 | 100.0 | 100.0 |
| Water for Kneading | 6.0. | 6.0 | 6.0 | 6.0 | 6.0 | 6.0 | 6.0. | 6.0 | 6.0 |
| Dissolution Rate | 4 | 3 | 3 | 3 | 1 | 1 | 2 | 1 | 8 |

TABLE 8

Effect of Fluorochemical Wetting Agents on Dissolution of WSG of Glyphosate

| | Example No. | | | | | | | | |
|---|---|---|---|---|---|---|---|---|---|
| Ingredients | 3-9 | 3-10 | 3-11 | 3-12 | 3-13 | 3-14 | 3-15 | 3-16 | Control |
| MON-8750 (88% ae) | 97.5 | 97.5 | 97.5 | 97.5 | 97.5 | 97.5 | 97.5 | 97.5 | 98.0 |
| Sorpol 7553 | 2.0 | 2.0 | 2.0 | 2.0 | 2.0 | 2.0 | 2.0 | 2.0 | 2.0 |
| Fluorad FC-83 (25% ai) | 0.5(ai) | — | — | — | — | — | — | — | — |
| Fluorad FC-85 (100% ai) | — | 0.5 | — | — | 13 | — | — | — | — |
| Fluorad FC-88 (100% ai) | — | — | 0.5(ai) | — | — | — | — | — | — |
| Fluorad FC-128 (50% ai) | — | — | — | 0.5(ai) | — | — | — | v— | — |
| Fluorad FC-135 (50% ai) | — | — | — | — | 0.5(ai) | — | — | — | — |
| Fluorad FC-170C (85% ai) | — | — | — | — | — | 0.5(ai) | — | — | — |
| Fluorad FC-430 (100% ai) | — | — | — | — | — | — | 0.5 | — | — |
| Fluorad FC-431 (50% ai) | — | — | — | — | — | — | — | 0.5(ai) | — |
| Total, w/w, % | 100.0 | 100.0 | 100.0 | 100.0 | 100.0 | 100.0 | 100.0 | 100.0 | 100.0 |
| Water for Kneading | 8.0 | 8.0 | 8.0 | 8.0 | 8.0 | 8.0 | 8.0 | 8.0 | 8.0 |
| Dissolution Rate | 2 | 2 | 4 | 1 | 1 | 1 | 3 | 1 | 8 |

TABLE 9

Effect of Fluorochemical Wetting Agents on Dissolution of WSG of Glyphosate

| | Example No. | | | | | | |
|---|---|---|---|---|---|---|---|
| Ingredients | 3-17 | 3-18 | 3-19 | 3-120 | 3-21 | 3-22 | Control |
| MON-8750 (88% ae) | 97.5 | 97.5 | 97.5 | 97.5 | 97.5 | 97.5 | 98.0 |
| Sorpol 7553 | 2.0 | 2.0 | 2.0 | 2.0 | 2.0 | 2.0 | 2.0 |
| ETOP ® EF-112 | 0.5 | — | — | — | — | — | — |
| ETOP ® EF-121 (100% ai) | — | 0.5 | — | — | — | — | — |
| ETOP ® EF-123A (100% ai) | — | — | 0.5 | — | — | — | — |
| ETOP ® EF-123B (100% ai) | — | — | — | 0.5 | — | — | — |
| ETOP ® EF-132 (100% ai) | — | — | — | — | 0.5 | — | — |
| ETOP ® EF-305 (100% ai) | — | — | — | — | — | 0.5 | — |
| Total, w/w, % | 100.0 | 100.0 | 100.0 | 100.0 | 100.0 | 100.0 | 100.0 |
| Water for Kneading | 7.5 | 7.5 | 7.5 | 7.5 | 7.5 | 7.5 | 8.0 |
| Dissolution Rate | 2 | 2 | 4 | 4 | 1 | 2 | 8 |

TABLE 10

Effect of Fluorochemical Wetting Agents on Dissolution of WSG of Glyphosate

| Ingredients | Example No. 3-23 | 3-24 | 3-25 | 3-26 | 3-27 | Control |
|---|---|---|---|---|---|---|
| MON-8750 (88% ae) | 97.5 | 97.5 | 97.5 | 97.5 | 97.5 | 98.0 |
| Sorpol 7553 | 2.0 | 2.0 | 2.0 | 2.0 | 2.0 | 2.0 |
| MEGAFAC F-120 (100% ai) | 0.5 | — | — | — | — | — |
| MEGAFAC F-142D (100% ai) | 0.5 | — | — | — | — | |
| MEGAFAC F-150 (100% ai) | — | 0.5 | — | — | — | |
| MEGAFAC F-177 (100% ai) | — | — | 0.5 | — | — | |
| MEGAFAC F-181 (100% ai) | — | — | — | 0.5 | — | |
| Total, w/w, % | 100.0 | 100.0 | 100.0 | 100.0 | 100.0 | 100.0 |
| Water for Kneading | 7.5 | 7.5 | 7.5 | 7.5 | 7.5 | 8.0 |
| Dissolution Rate | 1 | 2 | 2 | 3 | 3 | 8 |

TABLE 11

Effect of Fluorochemical Wetting Agents on Dissolution of WSG of Glyphosate

| Ingredients | Example No. 3-28 | 3-29 | 3-30 | 3-31 | Control |
|---|---|---|---|---|---|
| MON-8750 (88% ae) | 97.5 | 97.5 | 97.5 | 97.5 | 98.0 |
| Sorpol 7553 | 2.0 | 2.0 | 2.0 | 2.0 | 2.0 |
| UNIDYNE DS-102 (100% ai) | 0.5 | — | — | — | — |
| UNIDYNE DS-202 (100% ai) | — | 0.5 | — | — | — |
| UNIDYNE DS-401 (100% ai) | — | — | 0.5 | — | — |
| UNIDYNE DS-403 (100% ai) | — | — | — | 0.5 | — |
| Total, w/w, % | 100.0 | 100.0 | 100.0 | 100.0 | 100.0 |
| Water for Kneading | 7.5 | 7.5 | 7.5 | 7.5 | 8.0 |
| Dissolution Rate | 1 | 2 | 2 | 2 | 8 |

TABLE 12

Effect of Silicone Wetting Agents and Various Carriers on Dissolution of WSG of Glyphosate

| Ingredients | Example No. 3-32 | Control | 3-33 | Control | 3-34 | Control | 3-35 | Control | 3-36 | Control | 3-37 | Control |
|---|---|---|---|---|---|---|---|---|---|---|---|---|
| MON-8750 (86% ae) | 58 | 58 | 58 | 58 | 58 | 58 | 58 | 58 | 58 | 58 | 58 | 58 |
| Sorpol 7553 | 3 | 3 | 3 | 3 | 3 | 3 | 3 | 3 | 3 | 3 | 3 | 3 |
| Silwet L-77 | 4 | — | 4 | — | 4 | — | 4 | — | 4 | — | 4 | — |
| Sodium sulphate | 35 | 38 | — | — | — | — | — | — | — | — | — | — |
| Diammonium phosphate | — | — | 35 | 38 | — | — | — | — | — | — | — | — |
| Potassium sulfate | — | — | — | — | 35 | 38 | — | — | — | — | — | — |
| Potassium chloride | — | — | — | — | — | — | 35 | 38 | — | — | — | — |
| Urea | — | — | — | — | — | — | — | — | 35 | 38 | — | — |
| Starch | — | — | — | — | — | — | — | — | — | — | 35 | 38 |
| Total w/w, % | 100 | 100 | 100 | 100 | 100 | 100 | 100 | 100 | 100 | 100 | 100 | 100 |
| Water for Kneading | 6 | 8 | 6 | 8 | 6 | 8 | 6 | 8 | 6 | 8 | 6 | 8 |
| Dissolution Rate | 5 | 18 | 1 | 8 | 4 | 12 | 2 | 8 | 1 | 5 | 4 | 1 |

TABLE 13

Effect of Silicone and Fluorochemical Wetting Agents with Various Types of Surfactants on the Dissolution of Glyphosate

| Ingredients | 3-38 | Control | 3-39 | Control | 3-40 | Control | 3-41 | Control |
|---|---|---|---|---|---|---|---|---|
| MON-8750 (86% ae) | 21.0 | 21.0 | 41.0 | 41.0 | 21.0 | 21.0 | 21.0 | 21.0 |
| Silwet L-77 | — | — | — | — | 3.0 | — | 3.0 | — |
| Surflon S-113 (100% ai) | 1.0 | — | 1.0 | — | — | — | — | — |
| Amphitol 20N (35% ae) | 11.00(ai) | 4.0(ai) | — | — | — | — | — | — |
| Texopan K-1286 | — | — | 6.0 | 6.0 | — | — | — | — |
| Sorpol 7373 | — | — | — | — | 6.0 | 6.0 | — | — |
| Emalgen 809 | — | — | — | — | — | — | 6.0 | 6.0 |
| Ammonium sulfate powder | 74.0 | 76.0 | 26.0 | 27.0 | 70.0 | 73.0 | 70.0 | 73.0 |
| Diamonium phosphate | — | — | 26.0 | 26.0 | — | — | — | — |
| Total, w/w, % | 100.0 | 100.0 | 100.0 | 100.0 | 100.0 | 100.0 | 100.0 | 100.0 |
| Water for Kneading | 0.0 | 0.0 | 8.0 | 8.0 | 4.0 | 7.0 | 4.0 | 7.0 |
| Dissolution Rate | 1 | 6 | 1 | 5 | 2 | 8 | 1 | 7 |

Amphitobon = Amphoteric surfactant of alkyl dimethylamino oxide
Sorpol 7373 = Cationic surfactant of methyl dihydroxyethyl
Texopan K-1286 = Anionic surfactant of Sodium lauryl sulfate
Emalgen 809 = Nonionic surfactant of polyoxyethyl (EO = mole) nonyl phenylether

EXAMPLE 4

This example illustrates the preparation of improved water soluble granules (WSG) of glyphosate/ammonium sulfate with different Silwet L-77 concentrations and the dissolution rate of WSG with Silwet L-77 and without Silwet L-77 (control). WSG formulations according to the invention were made as follows. MON-8750 and ammonium sulfate powder were weighed into a pestle and mortar (automatic type: Nitto Model ANM-1000) and ground well for ½ hour. The Sorpol 7553 surfactant and Silwet L-77 wetting agent were then added and mixed for 5 minutes. Next, water for mixing and kneading was added; and the mixture was kneaded under room temperature for 10 minutes to make a dough like material. The dough like material from an automatic kneader was fed to an extruder equipped with a 1.0 mm extrusion port. The extruder product of this invention was typically a cylindrical shaped particle, having 1.0 mm diameter and having a length in the range from about 0.3 to about 5 mm.

After granulation, the drying of the extruder granules was carried out by using a fan dryer at 60° C. over a period of two hours.

Finally, the dried product was sieved by using a siever (micro siever model 100 type of TUTU1 Co.) equipped 12 and 48 mesh sieves. The results of the tested organosilicone wetting agents are given in Tables 14–16.

TABLE 14

Effect of A Silicone Wetting Agent on Dissolution of WSG of Glyphosate

| Ingredients | 4-1 | 4-2 | 4-3 | 4-4 | 4-5 | 4-6 | 4-7 | 4-8 | Control |
|---|---|---|---|---|---|---|---|---|---|
| MON-8750 (88% ae) | 21.00 | 21.00 | 21.00 | 21.00 | 21.00 | 21.00 | 21.00 | 21.00 | 21.00 |
| Sorpol 7553 | 5.95 | 5.90 | 5.70 | 5.50 | 5.00 | 4.00 | 2.00 | — | 6.00 |
| Silwet L-77 | 0.05 | 0.10 | 0.30 | 0.50 | 1.00 | 2.00 | 4.00 | 6.00 | — |
| Ammonium Sulfate powder | 73.00 | 73.00 | 73.00 | 73.00 | 73.00 | 73.00 | 73.00 | 73.00 | 73.00 |
| Total, w/w, % | 100.0 | 100.0 | 100.0 | 100.0 | 100.0 | 100.0 | 100.0 | 100.0 | 100.0 |
| Water for Kneading | 10.00 | 10.00 | 9.70 | 9.50 | 9.00 | 8.00 | 6.00 | 4.00 | 10.00 |
| Dissolution Rate | 4 | 3 | 2 | 2 | 2 | 2 | 1 | 1 | 8 |

TABLE 15

Effect of Various Ratios of a Surfactant and a Silicone Wetting Agent on the Dissolution of WSG of Glyphosate

| Ingredients | 4-9 | 4-10 | 4-11 | Control |
|---|---|---|---|---|
| NON-8750 (86% ae) | 42.00 (36% ae) | 42.00 | 42.00 | 42.00 |
| Sorpol 7553 | 1.00 | 1.00 | 1.00 | 1.00 |
| Silwet L-77 | 3.30 | 5.00 | 10.00 | — |
| Ammonium sulfate powder | 53.70 | 52.00 | 48.00 | 57.00 |
| Total, w/w, % | 100.0 | 100.0 | 100.0 | 100.00 |
| Water for Kneading | 6.70 | 4.00 | 1.00 | 9.00 |
| Dissolution Rate | 1 | 1 | 1 | 8 |

TABLE 16

Effect of Various Ratios of a Surfactant and a Silicone Wetting Agent on the Dissolution of WSG of Glyphosate

|  | Example No. | | |
| --- | --- | --- | --- |
| Ingredients | 4-12 | 4-13 | Control |
| MON-8750 (86% ae) | 58.10 (50% ae) | 58.10 | 58.10 |
| Sorpol 7553 | 2.00 | 2.00 | 2.00 |
| Silwet L-77 | 4.60 | 10.00 | — |
| Ammonium sulfate powder | 35.30 | 29.90 | 39.90 |
| Total, w/w, % | 100.00 | 100.00 | 100.00 |
| Water for Kneading | 3.40 | 1.00 | 8.00 |
| Dissolution Rate | 1 | 1 | 6 |

EXAMPLE 5

This example illustrates the preparation of improved water soluble granules (WSG) of glyphosate/ammonium sulfate with different Surflon S-145 concentration and the dissolution rate of WSG with Surflon S-145 wetting agent and without Surflon S-145 wetting agent (control). WSG formulations according to the invention were made from the following ingredients.

MON-8750 and ammonium sulfate powder were weighed into a pestle and a mortar (automatic type: Nitto model ANM-1000) and ground well for ½ hour. The Sorpol 7553 and Surflon S-145 were then added and mixed for 5 minutes. Next water for mixing and kneading was added and the mixture was kneaded under room temperature for 10 minutes to make dough like material. The dough like material from automatic type a pestle and a mortar was fed to an extruder (handy type) equipped 1.0 mm screen and the extruder product of this invention is typically a cylindrical shaped particle, having 1.0 mm diameter and having a length in the range from about 0.3 to about 5 mm.

After granulation, the drying of the extruder granules was carried out by using fan dryer at 60° C. over a period of two hours hours.

Finally, the dried product was sieved by using a siever (Micro Siever Model 100 type of TUTU1 Co.) equipped with 12 and 48 mesh sieves. The results of the tested wetting agents are given in Table 17.

EXAMPLE 6

This example illustrates the preparation of improved water soluble granules (WSG) of glyphosate with different Silwet L-77 concentrations and relates to the dissolution rate of WSG with Silwet L-77 and without Silwet L-77 (control). WSG formulations according to the invention were made from the following ingredients.

MON-8750 was weighed into a pestle and a mortar (automatic type: Nitto model ANM-1000) and ground well for ½ hour. The Sorpol 7553 and Silwet L-77 were then added and mixed for 5 minutes. Next, water for mixing and kneading was added; and the mixture was kneaded under room temperature for 10 minutes to make dough like material. The dough like material from automatic type a pestle and a mortar was fed to an extruder (handy type) equipped 1.0 mm screen and the extruder product of this invention is typically a cylindrical shaped particle, having 1.0 mm diameter and having a length in the range from about 0.3 to about 4 mm.

After granulation, the drying of the extruder granules was carried out by using fan dryer at 60° C. for a period of two hours.

Finally, the dried product was sieved by using a siever (Micro Siever Model 100 type of TUTU1 Co.) equipped 12 and 48 mesh sieves. The results of the tested wetting agents are given in Table 18.

TABLE 18

Effect of Various Amounts of Silicone Wetting Agents on Dissolution of WSG of Glyphosate

|  | Example No. | | | | |
| --- | --- | --- | --- | --- | --- |
| Ingredients | 6-1 | 6-2 | 6-3 | 6-4 | Control |
| MON-8750 (88% ae) | 85.0 (84% ae) | 82.0 (81% ae) | 87.0 (77% ae) | 70.0 (62% ae) | 87.0 (85% ae) |
| Sorpol 7553 | 3.0 | 3.0 | 3.0 | — | 3.0 |
| Silwet L-77 | 2.0 | 5.0 | 10.0 | 30.0 | — |
| Total, w/w, % | 100.0 | 100.0 | 100.0 | 100.0 | 100.0 |

TABLE 17

Effect of Varying Amounts of Fluorochemical Wetting Agent Agent on Dissolution Rate of WSG of Glyphosate

|  | Example No. | | | | | | |
| --- | --- | --- | --- | --- | --- | --- | --- |
| Ingredients | 5-1 | 5-2 | 5-3 | 5-4 | 5-5 | 5-6 | Control |
| MON-8750 (88% ae) | 21.00 | 21.00 | 21.00 | 21.00 | 21.00 | 21.00 | 21.00 (XXX) |
| Sorpol 7553 | 5.99 | 5.90 | 5.89 | 5.60 | 5.00 | 4.0 | 6.0 |
| Surflon S-145 (30% ai) | 0.01 (ai) | 0.10 (ai) | 0.20 (ai) | 0.40 (ai) | 1.00 (ai) | 2.00 (ai) | — |
| Ammonium sulfate powder | 73.00 | 73.00 | 73.00 | 73.00 | 73.00 | 73.00 | 73.00 |
| Total, w/w, % | 100.0 | 100.0 | 100.0 | 100.0 | 100.0 | 100.0 | 100.0 |
| Water for Kneading | 4.00 | 4.00 | 4.00 | 3.00 | 2.00 | 1.00 | 4.00 |
| Dissolution Rate | — | 2 | 2 | 2 | 1 | 1 | 8 |

TABLE 18-continued

Effect of Various Amounts of Silicone Wetting Agents on Dissolution of WSG of Glyphosate

| | Example No. | | | | |
|---|---|---|---|---|---|
| Ingredients | 6-1 | 6-2 | 6-3 | 6-4 | Control |
| Water for Kneading | 5.0 | 2.0 | 1.0 | 1.0 | 7.0 |
| Dissolution Rate | 2 | 1 | 1 | 1 | 7 |

EXAMPLE 7

Improved water soluble granular formulations of a commercial insecticide, fungicide and herbicide were prepared as follows.

99 parts of a commercial pesticidal water soluble powder (WSP) or water soluble granules (WSG) was mixed with 2 parts of Silwet L-77 until a uniform mixture was obtained, using an automatic type pestle and a mortar. To the resultant mixture 10 parts of water was added slowly. The mixture was kneaded well for 20 minutes to for a dough like material. The dough like material was extruded through a 1.0 mm extrusion port and cut to size. The extruded granules were dried with a fan dryer at 40–50° C. over a period of two hours and sieved with 12–48 mesh siever to give water soluble powders and granules of pesticide which dissolved remarkably fast compared with WSG of the same pesticide but without Silwet L-77.

The results of the tested wetting agents are given in Table 19.

TABLE 19

Effect of Silicone Wetting Agents on Dissolution of Other Pesticides

| | Example No. | | | | | | | |
|---|---|---|---|---|---|---|---|---|
| Ingredients | 7-1 | Control | 7-2 | Control | 7-3 | Control | 7-4 | Control |
| Paden water soluble powder (WSP) ® (Insecticide) | 98.0 | 100.0 | — | — | — | — | — | — |
| Cycloser water soluble granules (WSG) ® (Insecticide) | — | — | 98.0 | 100.00 | — | — | — | — |
| Polyoxin WSP ® (Fungicide) | — | — | — | — | 98.0 | 100.0 | — | — |
| Kusagard WSP ® (Herbicide) | — | — | — | — | — | — | 99.0 | 100.0 |
| Silwet L-77 | 2.0 | — | 2.0 | — | 2.0 | — | 2.0 | — |
| Total, w/w, % | 100.0 | 100.0 | 100.0 | 100.0 | 100.0 | 100.0 | 100.0 | 100.0 |
| Water for Kneading | 10.0 | 10.0 | 10.0 | 10.0 | 10.0 | 10.0 | 10.0 | 10.0 |
| Dissolution Rate | 1 | 16 | 2 | 28 | 3 | >30 | 4 | >30 |

EXAMPLE 8

Procedures for preparing water soluble granules of glyphosate/Bialaphos, glyphosate/basta, bialaphos and basta were as follows.

21 parts of MON-8750, 10.5 parts of Bialaphos, and 59.5 parts of ammonium sulfate powder were added to a pestle and a mortar and mixed well for 20 minutes. Next, to the resulting powder, 6 parts of Sorpol 7553 was added and mixed well for 20 minutes. Then, 3 parts of Silwet L-77 and 13 parts of water were added slowly. The mixture was kneaded at room temperature for 20 minutes to make a dough like material. The dough like material was extruded through a 1.0 mm extrusion port and the extrudate was cut to size. The resulting granules were dried with fan dryer at 50–60° C. over a period of two hours and sieved using a siever with 12 to 48 mesh siever to give improved water soluble granules of glyphosate/Bialaphos which dissolved remarkably fast compared with control WSG without Silwet L-77.

The results of the tested wetting agents are given in Tables 20–21.

TABLE 20

Effect of Silicone Wetting Agents on Glyphosate/Bialaphos and Glyphosate/Dicamba Formulations

| | Example No. | | | |
|---|---|---|---|---|
| Ingredients | 8-1 | Control | 8-2 | Control |
| MON-8750 (86% ae) | 21.0 | 21.0 | 21.0 | 21.0 |
| Na-Bialaphos (86% ai) | 10.5 | 10.5 | — | — |
| Na-Dicamba (86% ai) | — | — | 10.5 | 10.5 |
| Sorpol 7553 | 6.0 | 6.0 | 6.0 | 6.0 |
| Silwet L-77 | 3.0 | — | 3.0 | — |
| Ammonium Sulfate Powder | 58.5 | 62.5 | 58.5 | 62.5 |
| Total, w/w, % | 100.0 | 100.0 | 100.0 | 100.00 |
| Water for Kneading | 3.0 | 6.0 | 3.0 | 6.0 |
| Dissolution Rate | 1 | 7 | 1 | 8 |

TABLE 21

Effect of Silicone Surfactant on Bialaphos and Gliphosinate WSG

| | Example No. | | | |
|---|---|---|---|---|
| Ingredients | 8-3 | Control | 8-4 | Control |
| Na-Bialaphos (80% ai) | 21.0 | 21.0 | — | — |
| NH4-Glyphosinate | — | — | 21.0 | 21.0 |

TABLE 21-continued

Effect of Silicone Surfactant on Bialaphos and Gliphosinate WSG

| | Example No. | | | |
|---|---|---|---|---|
| Ingredients | 8-3 | Control | 8-4 | Control |
| Sorpol 7553 | 6.0 | 6.0 | 6.0 | 6.0 |
| Silwet L-77 | 3.0 | — | 3.0 | — |
| Ammonium sulfate powder | 70.0 | 73.0 | 70.0 | 73.0 |
| Total, w/w, % | 100.0 | 100.0 | 100.0 | 100.00 |
| Water for Kneading | 3.0 | 6.0 | 3.0 | 6.0 |
| Dissolution Rate | 2 | 8 | 2 | 8 |

EXAMPLE 9

This example illustrates a preparation of the granules using a spray dryer and mixer.

16.0 parts of MON-8750, 20.0 part of Sorpol 5115, 61.0 parts of ammonium sulfate and 300 parts of water were added into the vessel and mixed well with heating to make a clear solution. The resulting solution was evaporated using a spray dryer to give a spray dried product of glyphosate, surfactant and ammonium sulfate.

Next, 97 parts of the spray dried product was charged to a vertical agitation mixing type granulator, and mixed with spraying of 60 parts of 50% Silwet L-77 water solution for 10 minutes. The granules were dried in a laboratory fluid bed dryer and sieved with a 12 and 80 mesh siever.

The results of the tested wetting agents are given in Table 22.

TABLE 22

Effect of Silicone Wetting Agent on Glyphosate WSG
Prepared with Spray Dryer and Vertical Granulator

| | Example No. | |
|---|---|---|
| Ingredients | 9 | Control |
| MON-8750 (86% ae) | 16.0 | 16.0 |
| Sorpol 5115 | 20.0 | 20.0 |
| Silwet L-77 | 3.0 | — |
| Ammonium sulfate | 61.0 | 64.0 |
| Total, w/w, % | 100.0 | 100.0 |
| Water for Granulation | 3.0 | 6.0 |
| Particle Size (mesh) | 12–80 | 12–80 |
| Dissolution Rate | 8 | >30 |

EXAMPLE 10

It was also found that Silwet L-77 wetting agent improves the dissolution rate of trimethylsulfonium glyphosate significantly. Silwet L-77 also decreases the dissolution rate of water soluble salt of glyphosate, e.g., Na salt, K salt, ammonium salt, trimethylsulfonium salt, etc.

Considering the mechanism of the dissolution improvement by Silwet L-77 (increase of the wettability with water), the effect of Silwet L-77 is believed to be independent of the salt.

The results of this example are given in Table 23.

TABLE 23

| | Example No. | | | |
|---|---|---|---|---|
| Ingredients | 10-1 | Control | 10-2 | Control |
| Trimethylsulfonium glyphosate (tech) | 10.5 | 10.5 | 21.0 | 21.0 |
| Sorpol 7553 | 3.0 | 6.0 | 3.0 | 6.0 |
| Silwet L-77 | 3.0 | — | 3.0 | — |
| Ammonium sulfate powder | 83.5 | 83.5 | 73.0 | 73.0 |
| Total w/w % | 100.0 | 100.0 | 100.0 | 100.0 |
| Water for kneading | 4.0 | 4.0 | 2.0 | 2.0 |
| Dissolution rate in water | 1 | 3 | 3 | 8 |

EXAMPLE 11

It was also found that Silwet L-77 improves the dissolution rate of the 1,1,3,3-tetramethyl-guanidinium salt of glyphosate significantly. The results of this example are in Table 24.

TABLE 24

Effect of Silwet L-77 on 1,1,3,3-tetramethyl-
guanidinium glyphosate/Sorpol/AS WSG

| | Example No. | |
|---|---|---|
| Ingredients | 11-1 | Control |
| 1,1,3,3 tetramethylguanidinium glyphosate (Tech) | 10.5 | 10.5 |
| Sorpol 7553 | 2.0 | 5.0 |
| Silwet L-77 | 3.0 | — |
| Ammonium sulfate powder | 84.5 | 84.5 |
| Total w/w % | 100.0 | 100.0 |
| Water for kneading | 5.0 | 5.0 |
| Dissolution Rate | 1 | 5 |

EXAMPLE 12

Water dispersible granules (WDG) of formulated glyphosate and Goal mixtures were prepared as follows.

A vessel was charged with 8 parts of water, 3.2 parts of Goal herbicide technical and 1.5 parts of Sorpol 3005C. The vessel was heated gently in a water bath. The mixture was stirred for ½ hour at 60° C. to make a suspension. The suspension was mixed with 37.7 parts of MON-8750 and 53 parts of ammonium sulfate powder in a pestle and a mortar. The mixture was mixed with various amounts of Silwet L-77 and kneaded for 20 minutes to make dough like materials. The dough like material was extruded through a 1.0 mm extrusion port and the extrudate was cut to size. The resulting granules were dried with a fan dryer at 60–70° C. and sieved with 12–48 mesh sieves.

The results of this example are given in Table 25.

TABLE 25

Effect of Silwet L-77 on Glyphosate/Goal ® WSG

| | Example No. | | |
|---|---|---|---|
| Ingredients | 13-1 | 13-2 | Control |
| MON-8750 (88% ae) | 37.7 | 41.0 | 37.7 |
| Goal Tech (70% ai) | 3.2 | 3.4 | 3.2 |
| Sorpol 3005C | 1.5 | 2.0 | 1.5 |

TABLE 25-continued

Effect of Silwet L-77 on Glyphosate/Goal ® WSG

| | Example No. | | |
|---|---|---|---|
| Ingredients | 13-1 | 13-2 | Control |
| Silwet L-77 | 4.6 | 1.0 | — |
| Ammonium sulfate powder | 53.0 | 53.6 | 57.6 |
| Total, w/w, % | 100.0 | 100.0 | 100.0 |
| Water for Kneading | 8.0 | 8.0 | 8.0 |
| Dispersion Rate | 2 | 2 | >10 |

EXAMPLE 13

It was also found that Silwet L-77 improves the dissolution rate of glyphosate sulfonimide derivative (M.K. MAO NBP 4130620 J. A. Sikorski Jan. 18, 1989), significantly. L-77 increases the dissolution rate of salts of glyphosate sulfonimide, e.g.,

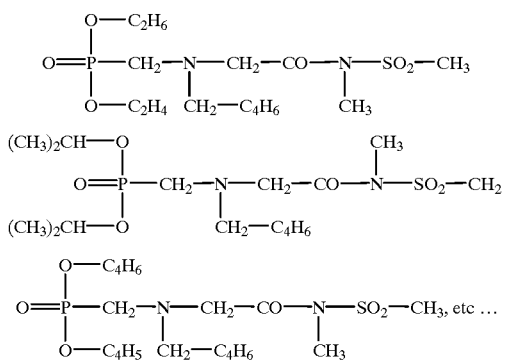

21 g of glyphosate sulfonimide derivatives, 71 g of ammonium sulfate powder and 6 g of Sorpol 7553 (Tallowamine EO 15 mole adduct) were added together and mixed for about 10 minutes.

The resultant mixture was a solid powder. About 6 g of water was added to the admixture and the mixture was kneaded at room temperature for 15 minutes. The resultant mixture was a dough like material. The dough was then fed into the extruder and is extruded through holes of 1.0 mm diameter. The extruded granules (diameter 1.0 mm, length 1–5 mm) were dried in a fan electrical oven over a period of 1–2 hours at 60–70° C. The dried granule was screened by a shifter to 12/48 mesh.

The results of this example are given in Table 26.

TABLE 26

Effect of Silicone Wetting Agent on Glyphosate Sulfonimide WSG

| | Example No. | |
|---|---|---|
| Ingredients | 15 | Control |
| Glyphosate Sulfonimide derivatives | 21.0 g | 21.0 g |
| Sorpol 7553 | 6.0 | 6.0 |

TABLE 26-continued

Effect of Silicone Wetting Agent on Glyphosate Sulfonimide WSG

| | Example No. | |
|---|---|---|
| Ingredients | 15 | Control |
| Silwet L-77 | 2.0 | — |
| Ammonium sulfate powder | 71.0 | 73.0 |
| Total w/w % | 100.0 | 100.0 |
| Water for kneading | 6.0 | 8.0 |
| Dispersion rate in water | 5 | >10 |

EXAMPLE 14

Improvements of dispersibility of water dispersible granule (WDG) of glyphosate, such as mixtures—glyphosate/Sumitomo S-275 WDG and Gly-phosate/Atrazine WDG, were noted. The dispersibility in water increases significantly, because the gly-phosate salt dissolves quickly.

MON-8740 (21 g), S-275 tech (2 g) and ammonium sulfate (70 g) were mixed in a mortar and was ground with a pestle for 20 minutes.

Then, surfactant (Sorpol 7553, 6 g) surflon S-145 (1 g as ai), and water (4 g) were added to the mixture and mixed in a kneader for 10 minutes. The resultant dough like material was extruded through holes of 1 mm diameter and the extrudate was cut to a length of 1–5 mm. The granules were dried in a fan oven for 2 hours at 50° C.

The results of this example are given in Tables 27–28.

TABLE 27

Effect of Fluorochemical Wetting Agent on the Dispersion Rate of Glyphosate/Sumitomo S-275 (Herbicide) Water Dispersible Granules (WDG)

| | Example No. | |
|---|---|---|
| Ingredients | 14-1 | Control |
| MON-8750 (88% ae) | 21.0 | 21.0 |
| Sorpol 7553 | 6.0 | 6.0 |
| Sumitomo S-275 (97% ai) | 2.0 | 2.0 |
| Surflon S-145 (30% ai) | 1.0 | — |
| Ammonium sulfate powder | 70.0 | 71.0 |
| Total w/w % | 100.0 | 100.0 |
| Water for kneading | 4.0 | 4.0 |
| Dispersion Rate | 1 | >20 |

TABLE 28

Effect of Fluorochemical Wetting Agents on Glyphosate/Sumitomo S-275 (Herbicide) WDG

| Ingredients | Example No. | | | | | | |
|---|---|---|---|---|---|---|---|
| | 14-2 | 14-3 | 14-4 | 14-5 | 14-6 | 14-7 | Control |
| MON-8750 (88% ae) | 21.0 | 21.0 | 21.0 | 21.0 | 21.0 | 21.0 | 21.0 |
| Sorpol 7553 | 6.0 | 6.0 | 6.0 | 6.0 | 6.0 | 6.0 | 6.0 |
| Sumitomo S-275 Tech (97% ai) | 2.0 | 2.0 | 2.0 | 2.0 | 2.0 | 2.0 | 2.0 |
| Surflon S-111 (30% ai) | 1.0 (ai) | — | — | — | — | — | — |
| Surflon S-112 (15% ai) | — | 1.0 (ai) | — | — | — | — | — |
| Surflon S-113 (30% ai) | — | — | 1.0 (ai) | — | — | — | — |
| Surflon S-121 (30% ai) | — | — | — | 1.0 (ai) | — | — | — |
| Surflon S-131 (30% ai) | — | — | — | — | 1.0 (ai) | — | — |
| Surflon S-135 (30% ai) | — | — | — | — | — | 1.0 (ai) | — |
| Surflon S-145 (30% ai) | — | — | — | — | — | — | — |
| Ammonium Sulfate Powder | 70.0 | 70.0 | 70.0 | 70.0 | 70.0 | 70.0 | 71.0 |
| Total, w/w, % | 100.0 | 100.0 | 100.0 | 100.0 | 100.0 | 100.0 | 100.0 |
| Water for Kneading | 4.0 | 2.0 | 4.0 | 4.0 | 4.0 | 4.0 | 4.0 |
| Dispersion Rate | 3 | 4 | 2 | 2 | 2 | 2 | >20 |

EXAMPLE 14

The effect of Silwet L-77 on the dispersion rate of glyphosate/atrazine WDG was tested. The results of this example are given in Table 29.

TABLE 29

| Ingredients | Example No. | |
|---|---|---|
| | 14 | Control |
| MON-8750 (88% ae) | 16.2 | 16.2 |
| Sorpol 7553 | 5.0 | 5.0 |
| Atrazine Tech. (95% ai) | 20.0 | 20.0 |
| Silwet L-77 | 3.0 | — |
| Ammonium sulfate | 55.8 | 58.0 |
| Total w/w % | 100.0 | 100.0 |
| Water for kneading | 5.0 | 8.0 |
| Dispersion Rate | 8 | >20 |

EXAMPLE 16

With the practice of the present invention improvements of the dispersibility of wettable powder (WP) were noted. The results of this example are set forth in Table 30. A mixture of a herbicide and a fungicide was used.

Dithane® Z-78 fungicide wettable powder (98 g) and Silwet L-77 (2 g) were mixed and ground together in a mortar for one hour.

The mixed WP dispersed more quickly than the mixture prepared without L-77.

TABLE 30

Effect of Silwet L-77 on the Dispersion Rate of Wettable Powder (WP)

| Ingredient | Example No | | | |
|---|---|---|---|---|
| | 16-1 | Control | 16-2 | Control |
| Dithane Z-78 ® WP | 98.0 | 100.0 | — | — |
| GL-861 WP | — | — | 98.0 | 100.0 |
| Silwet L-77 | 2.0 | — | 2.0 | — |
| Total w/w % | 100.0 | 100.0 | 100.0 | 100.0 |
| Dispersion Rate | 5 | 150 | 6 | 18 |

GL-861 WP is a glyphosate-linuron wettable powder mixture.

What is claimed is:

1. A solid composition in granular form comprising a herbicidally effective amount of glyphosate in water soluble form, an ethoxylated alkylamine surfactant in a weight ratio of glyphosate acid equivalent to ethoxylated alkylamine surfactant of about 2.4 to about 42.2 and about 0.1% to about 5.0% by weight of a silicone block copolymer having the formula:

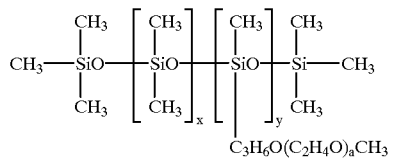

wherein x is 0 or 1, y is 1–5, and a is 5–20, whereby the dissolution rate in water of the said composition is substantially enhanced as compared to the dissolution rate thereof without the presence of the silicone block copolymer.

2. The composition of claim 1 wherein x is 0, y is 1–5, and a is 5–20.

3. The composition of claim 1 wherein the ethoxylated alkylamine contains about 15–20 ethylene oxide units.

4. The composition of claim 1 wherein the water soluble glyphosate is in the form of ammonium glyphosate.

* * * * *

UNITED STATES PATENT AND TRADEMARK OFFICE
CERTIFICATE OF CORRECTION

PATENT NO. : 6,051,533
DATED : April 18, 2000
INVENTOR(S) : Akira Kajikawa, Masuo Kuchikata, Ronald O. Richardson, Tatsuo Sato It is certified that error appears in the above-identified patent and that said Letters Patent is hereby corrected as shown below:

Claim 3, line 4, after "alkylamine" insert --is an ethoxylated tallowamine--.

Signed and Sealed this

Thirteenth Day of March, 2001

Attest:

NICHOLAS P. GODICI

*Attesting Officer*  *Acting Director of the United States Patent and Trademark Office*